US010993917B2

(12) United States Patent
Kurisawa et al.

(10) Patent No.: US 10,993,917 B2
(45) Date of Patent: May 4, 2021

(54) NANOCOMPLEX

(71) Applicant: AGENCY FOR SCIENCE, TECHNOLOGY AND RESEARCH, Singapore (SG)

(72) Inventors: Motoichi Kurisawa, Singapore (SG); Ki Hyun Bae, Singapore (SG); Susi Tan, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 16/343,434

(22) PCT Filed: Dec. 29, 2017

(86) PCT No.: PCT/SG2017/050658
§ 371 (c)(1),
(2) Date: Apr. 19, 2019

(87) PCT Pub. No.: WO2018/124970
PCT Pub. Date: Jul. 5, 2018

(65) Prior Publication Data
US 2019/0262271 A1    Aug. 29, 2019

(30) Foreign Application Priority Data

Dec. 30, 2016 (SG) .............. 10201610979T

(51) Int. Cl.
| A61K 9/50 | (2006.01) |
| A61P 35/00 | (2006.01) |
| A61K 47/61 | (2017.01) |
| A61K 33/243 | (2019.01) |
| A61K 9/51 | (2006.01) |
| A61K 31/282 | (2006.01) |
| A61K 31/41 | (2006.01) |
| A61K 31/555 | (2006.01) |
| A61K 47/69 | (2017.01) |
| A61K 31/665 | (2006.01) |

(52) U.S. Cl.
CPC .......... *A61K 9/5036* (2013.01); *A61K 9/5123* (2013.01); *A61K 31/282* (2013.01); *A61K 31/41* (2013.01); *A61K 31/555* (2013.01); *A61K 31/665* (2013.01); *A61K 33/243* (2019.01); *A61K 47/61* (2017.08); *A61K 47/6907* (2017.08); *A61P 35/00* (2018.01)

(58) Field of Classification Search
None
See application file for complete search history.

(56) References Cited

U.S. PATENT DOCUMENTS

| 2002/0128512 A1* | 9/2002 | Bulpitt .................. C07C 323/25 564/252 |
| 2011/0044992 A1 | 2/2011 | Ying et al. |
| 2012/0148567 A1 | 6/2012 | Kurisawa et al. |
| 2013/0131283 A1 | 5/2013 | Wang et al. |

FOREIGN PATENT DOCUMENTS

| WO | WO-2011/112156 A1 | 9/2011 |
| WO | WO2015171079 | * 11/2015 |

OTHER PUBLICATIONS

Greene et al., Stability of cisplatin in aqueous solution, American Journal of Hospital Pharmacy, vol. 36, Issue 1, Jan. 1, 1979, Abstract, https://academic.oup.com/ajhp/article-abstract/36/1/38/5196072 (Year: 1979).*
Verschraagen et al., Simultaneous determination of intact cisplatin and its metabolite monohydrated cisplatin in human plasma, Journal of Chromatography B, 772 (2002) 273-281 (Year: 2002).*
Wang et al., "Amphiphilic Carboxymethyl Chitosan-quercetin Conjugate With P-gp Inhibitory Properties for Oral Delivery of Paclitaxel", Biomaterials 35, 2014, pp. 7654-7665.
Search Report and Written Opinion in International Application No. PCT/SG2017/050658 dated Feb. 28, 2018.

* cited by examiner

*Primary Examiner* — Jennifer A Berrios
(74) *Attorney, Agent, or Firm* — Marshall, Gerstein & Borun LLP

(57) ABSTRACT

There is provided a nanocomplex having a core-shell structure. The shell of the nanocomplex comprises a functionalized hyaluronic acid while the core of the nanocomplex comprises a flavonoid encapsulating a metal-containing compound. Preferably, the flavonoid is epigallocatechin gallate (EGCG) and the hyaluronic acid is thiol-functionalized and subsequently conjugated to the flavonoid. There is also provided a method of forming the nanocomplex, a pharmaceutical composition comprising the nanocomplex, medical uses of the nanocomplex and a method of treating a patient, preferably with cancer using the nanocomplex.

20 Claims, 19 Drawing Sheets

[Fig. 1]
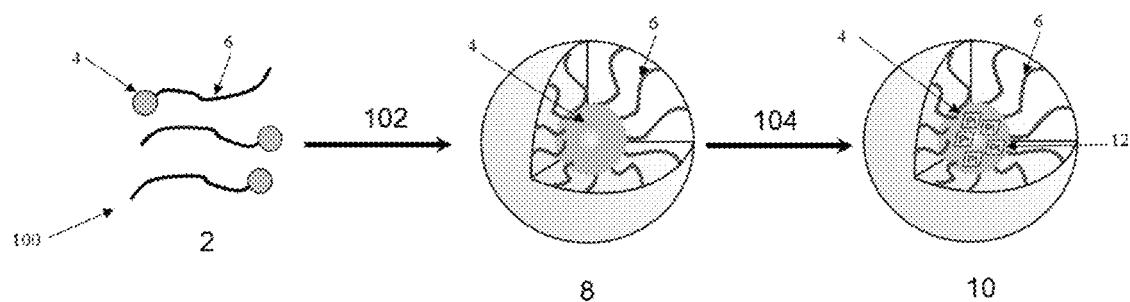

[Fig. 2A-1]
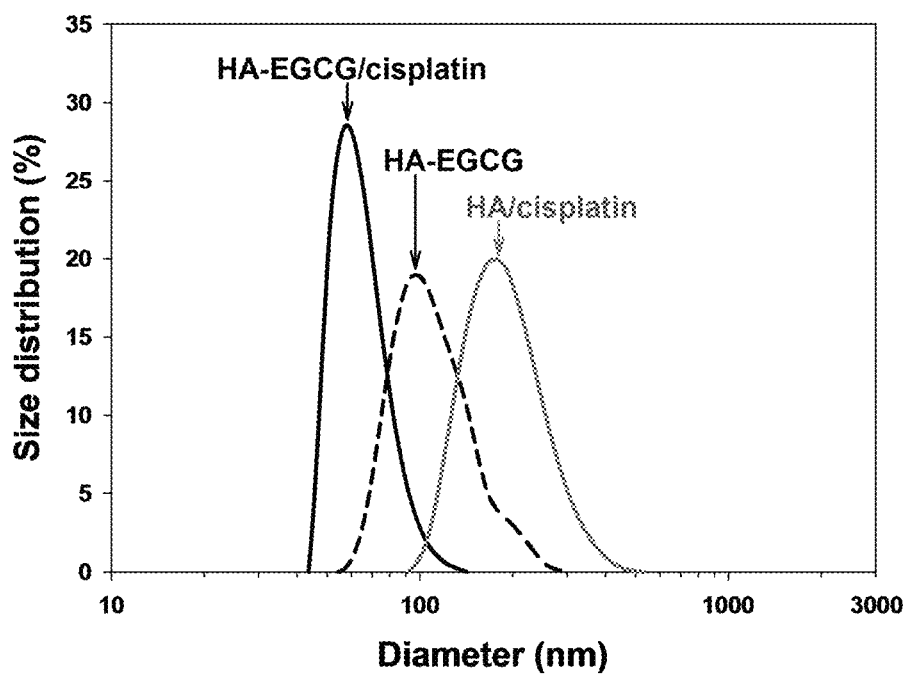
[Fig. 2A-2]
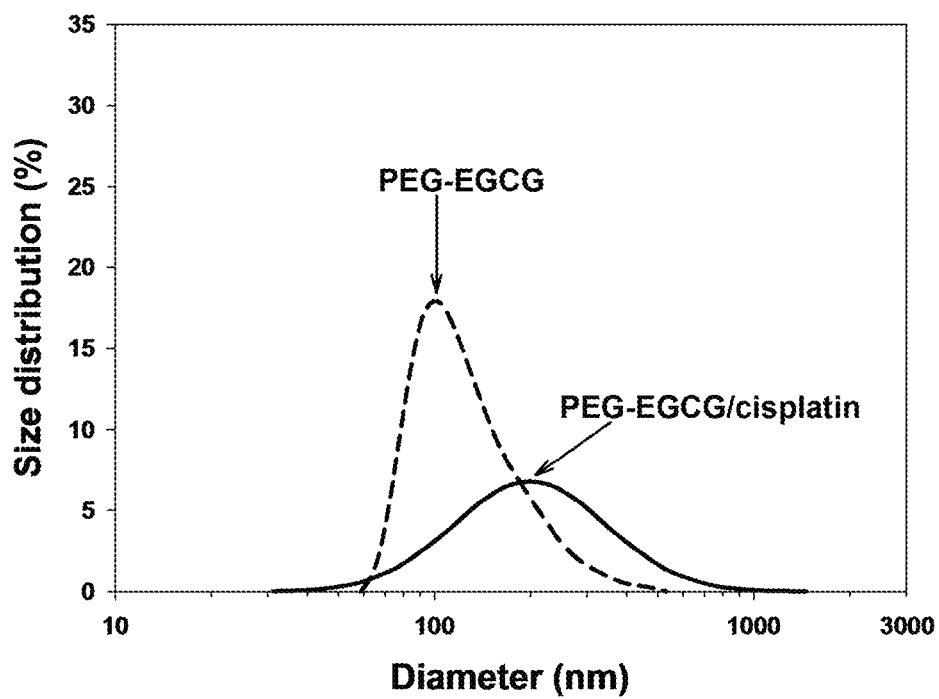

[Fig. 2B]
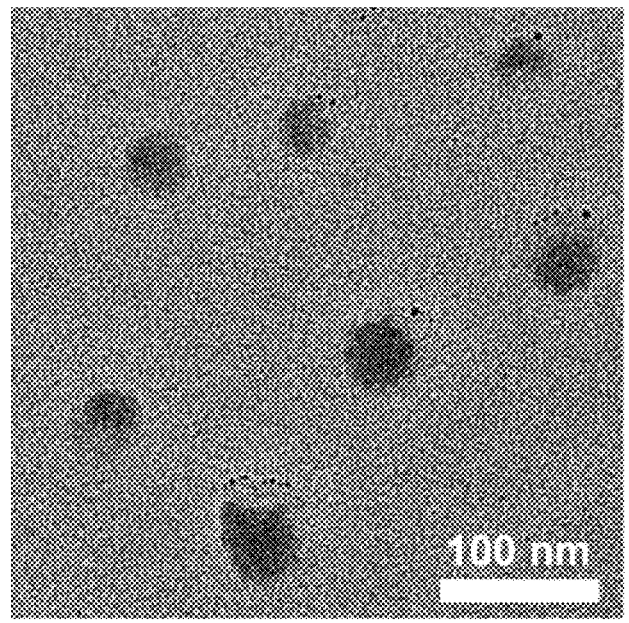
[Fig. 2C]
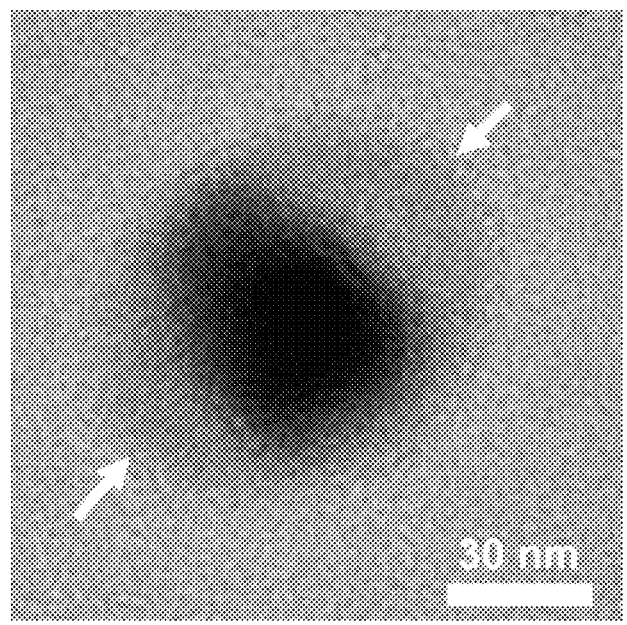

[Fig. 2D]
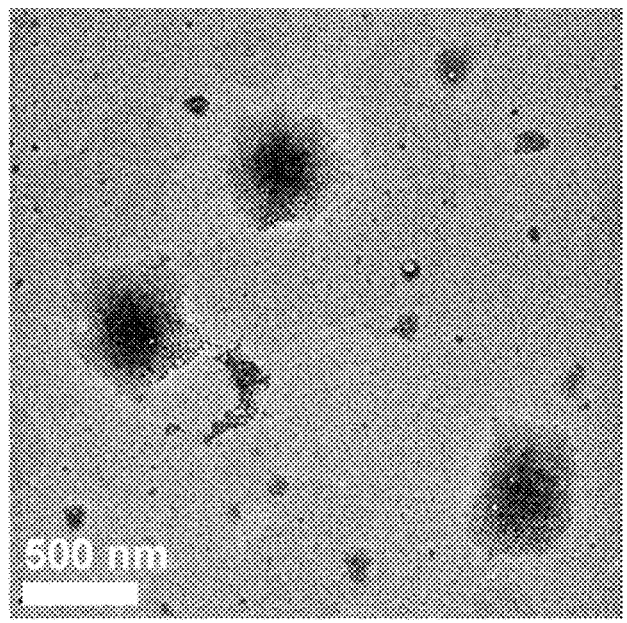
[Fig. 2E]
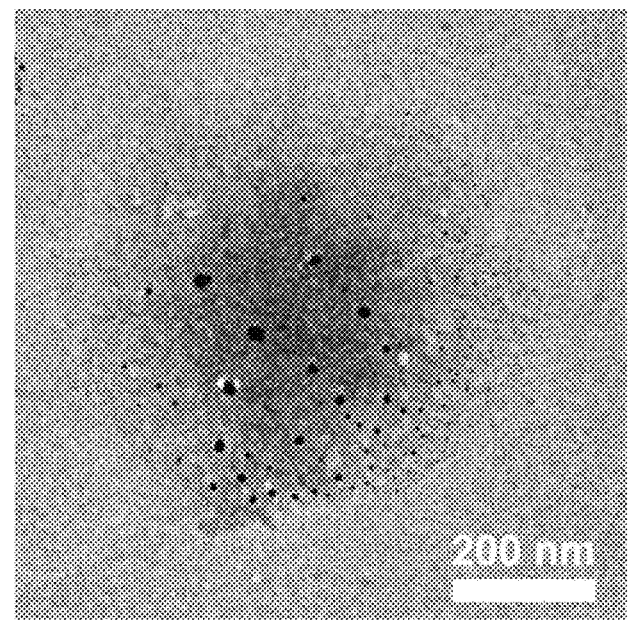

[Fig. 3A]
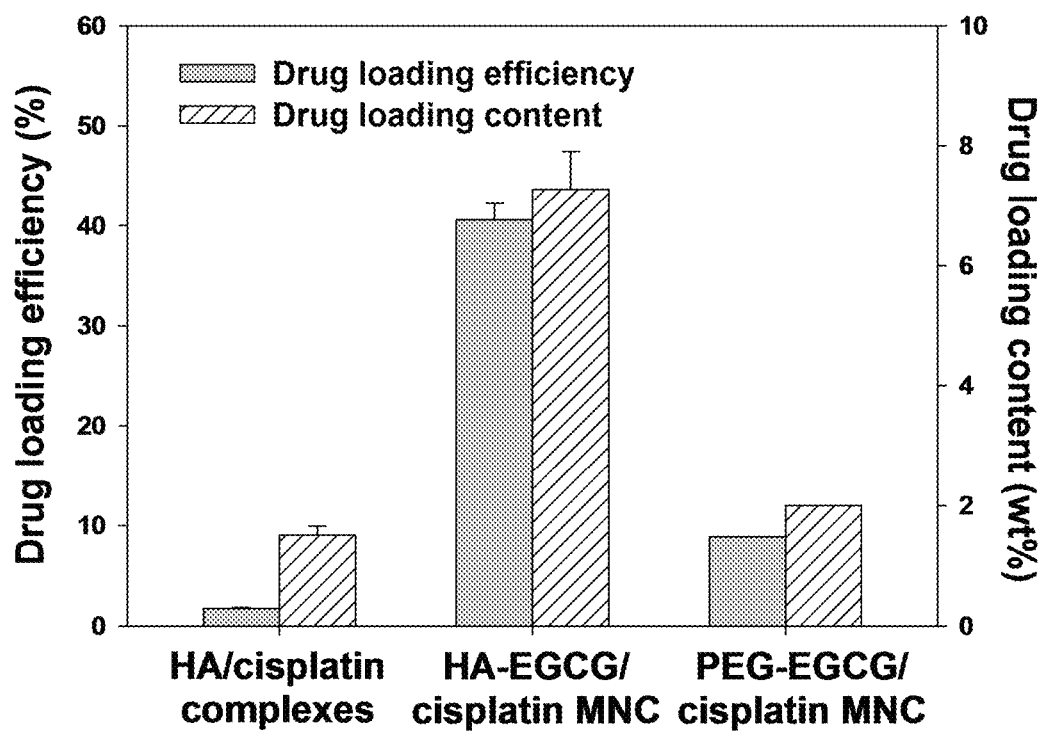

[Fig. 3B-1]
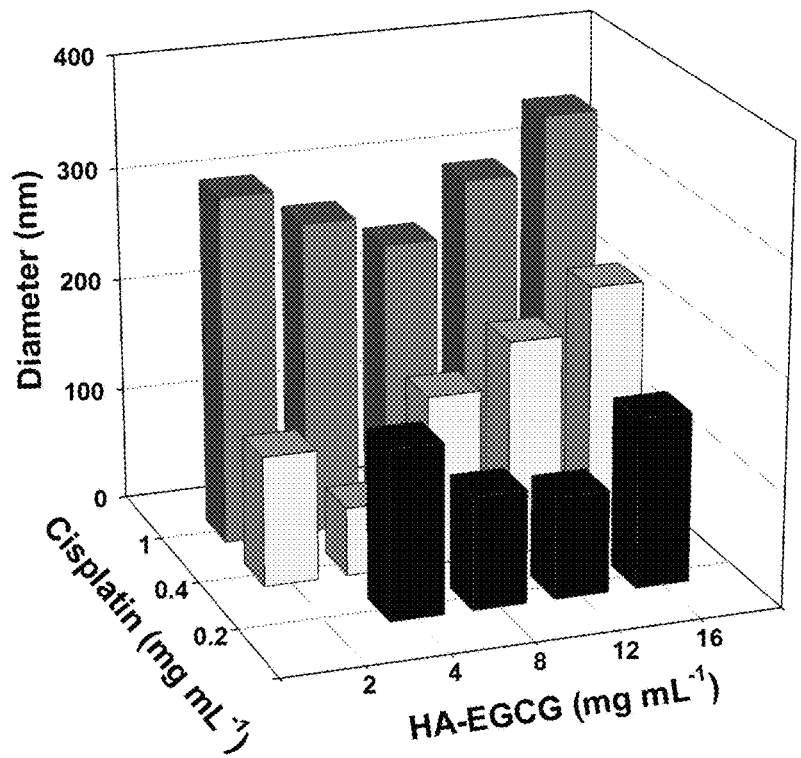
[Fig. 3B-2]
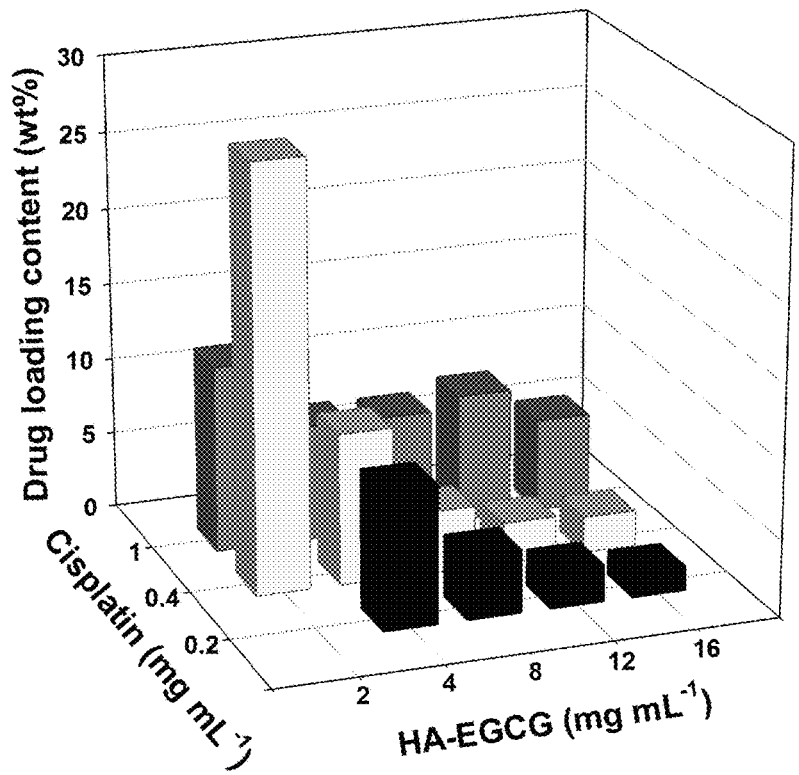

[Fig. 4]
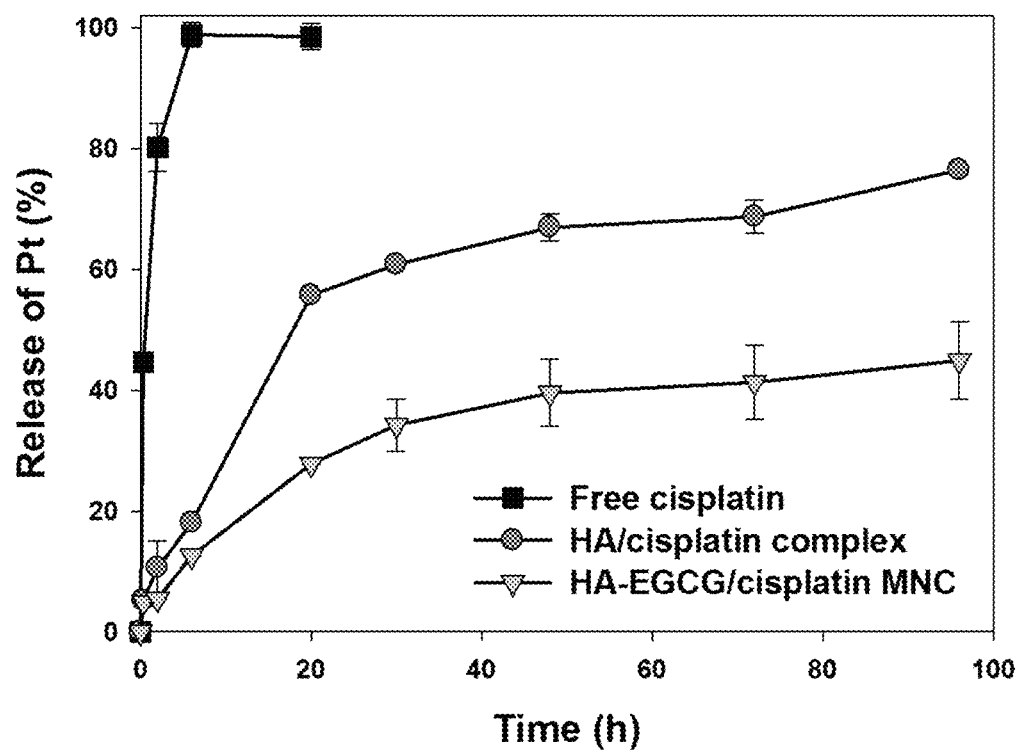

[Fig. 5]
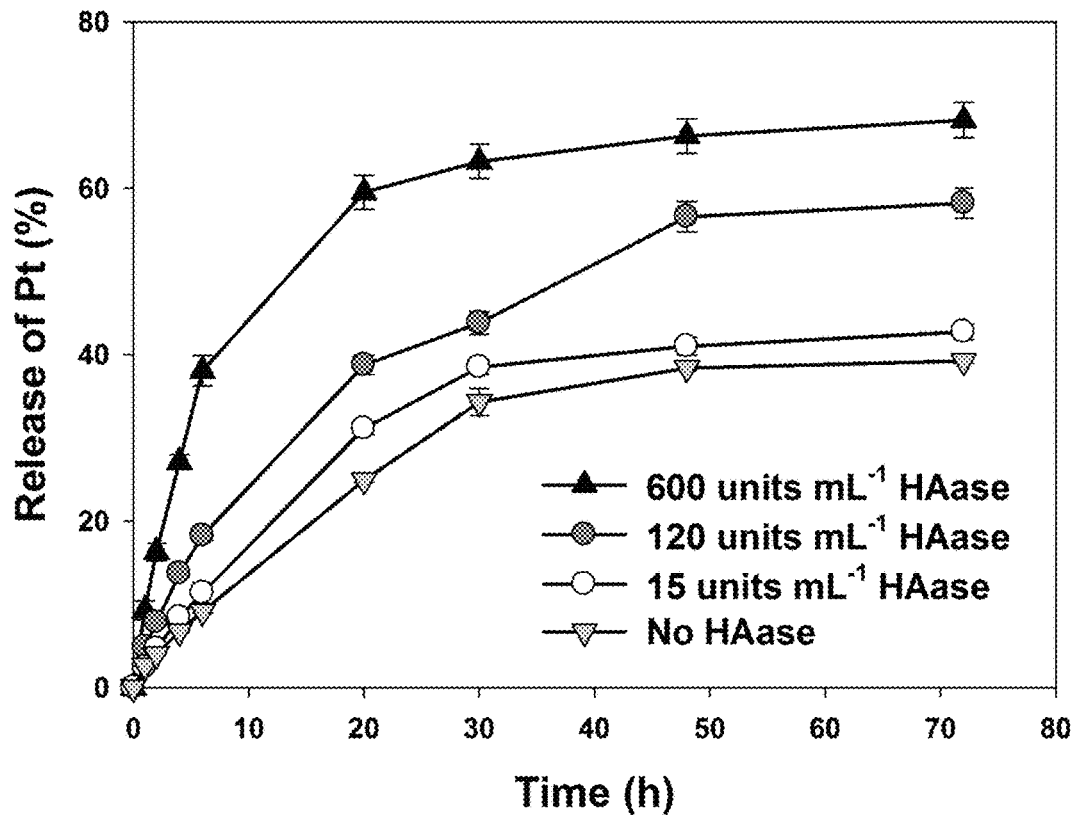
[Fig. 6]
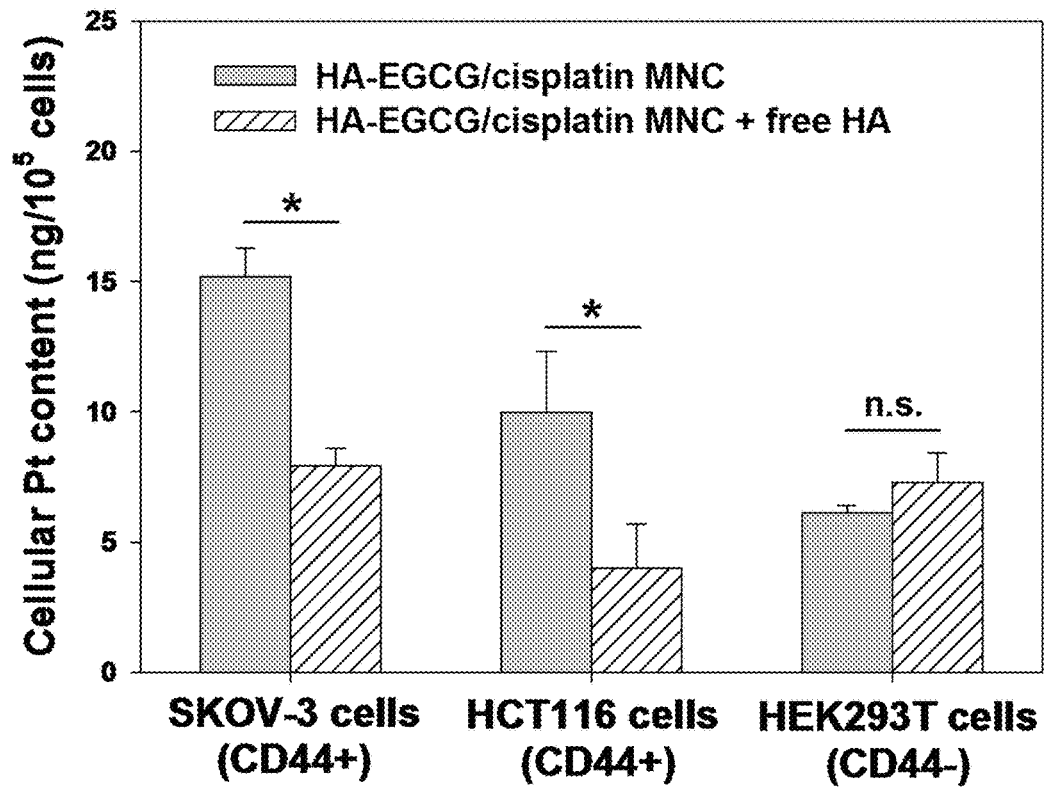

[Fig. 7]
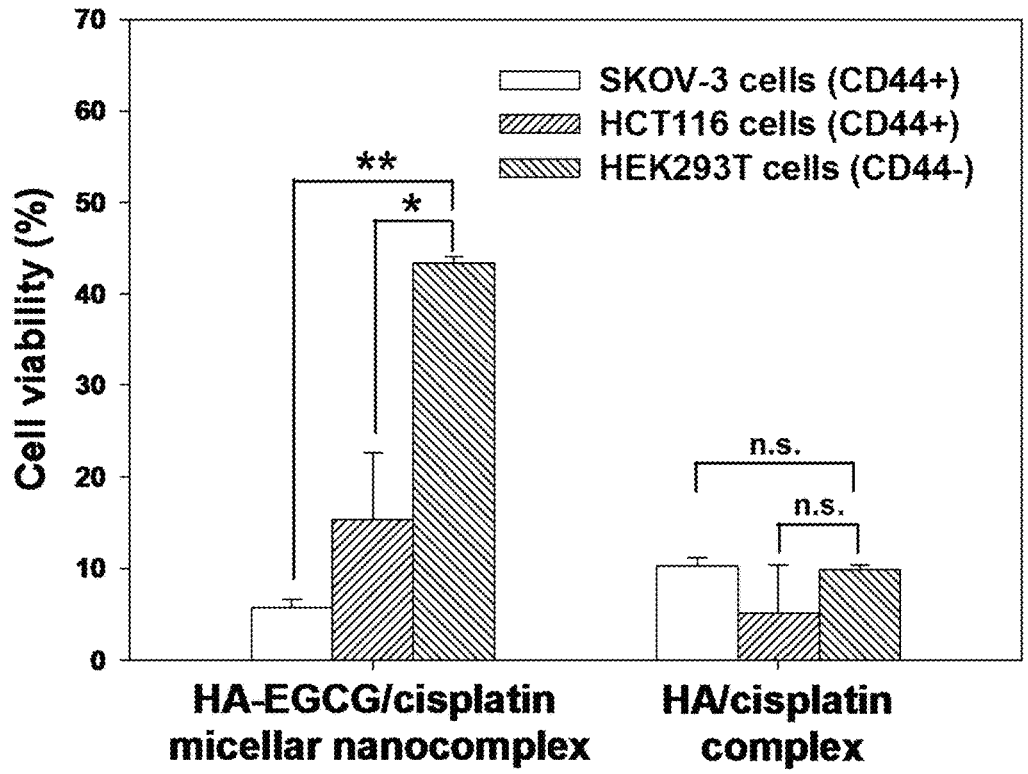
[Fig. 8]
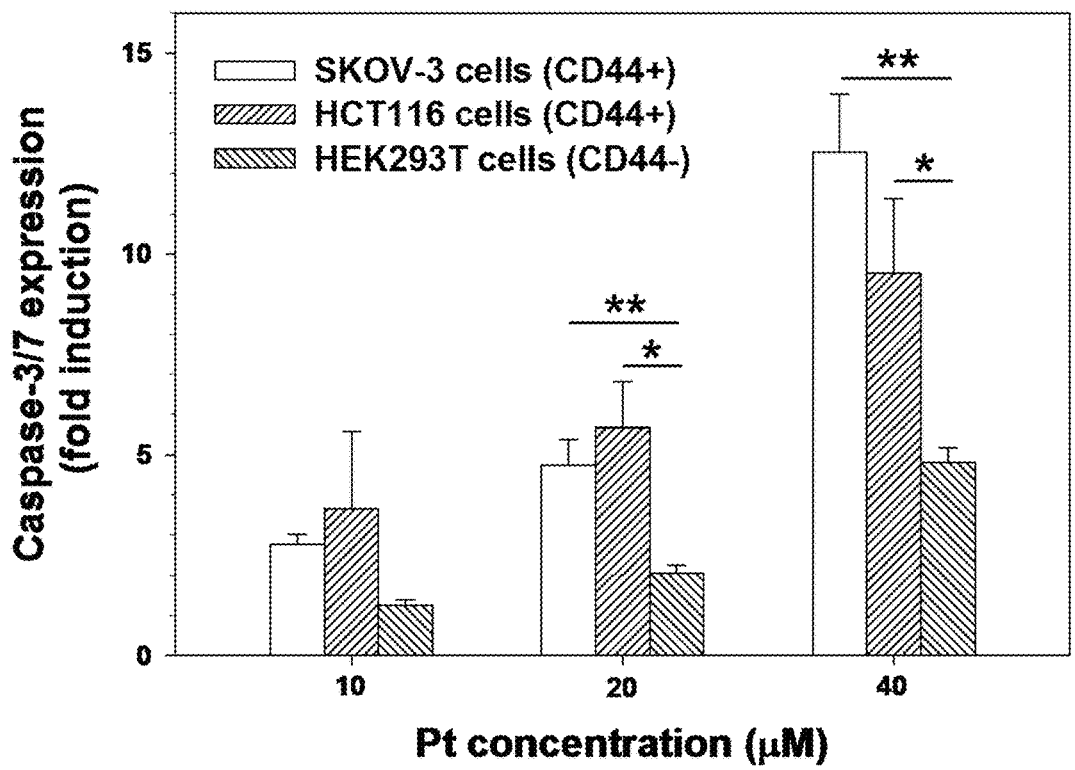

[Fig. 9]
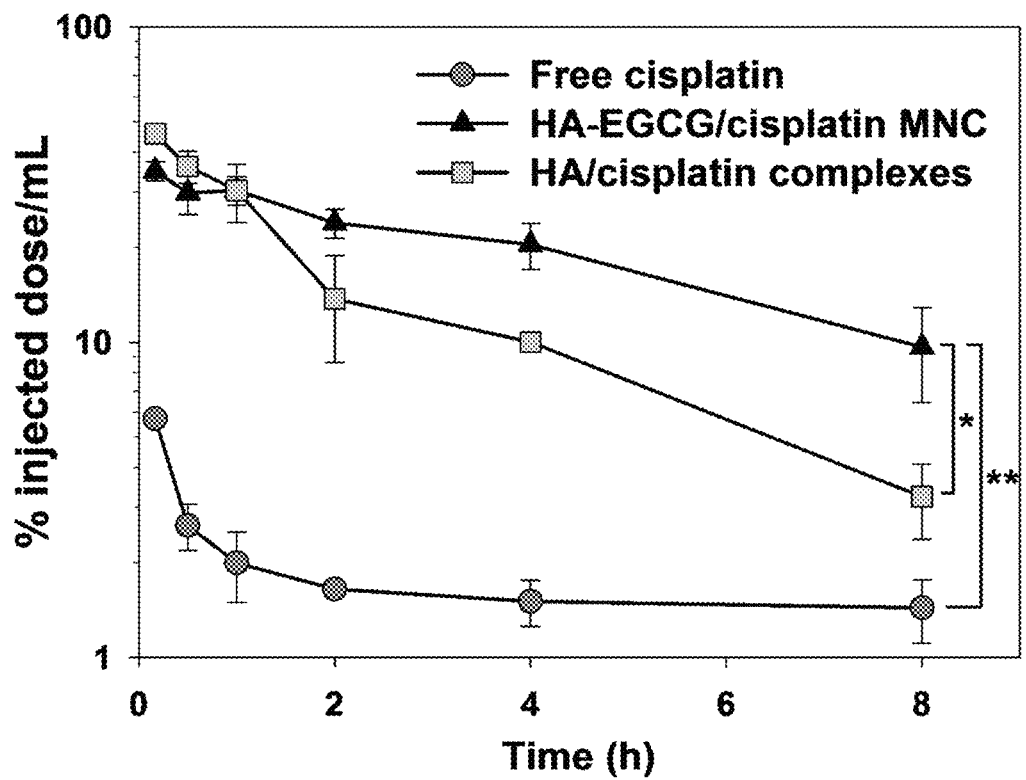
[Fig. 10]
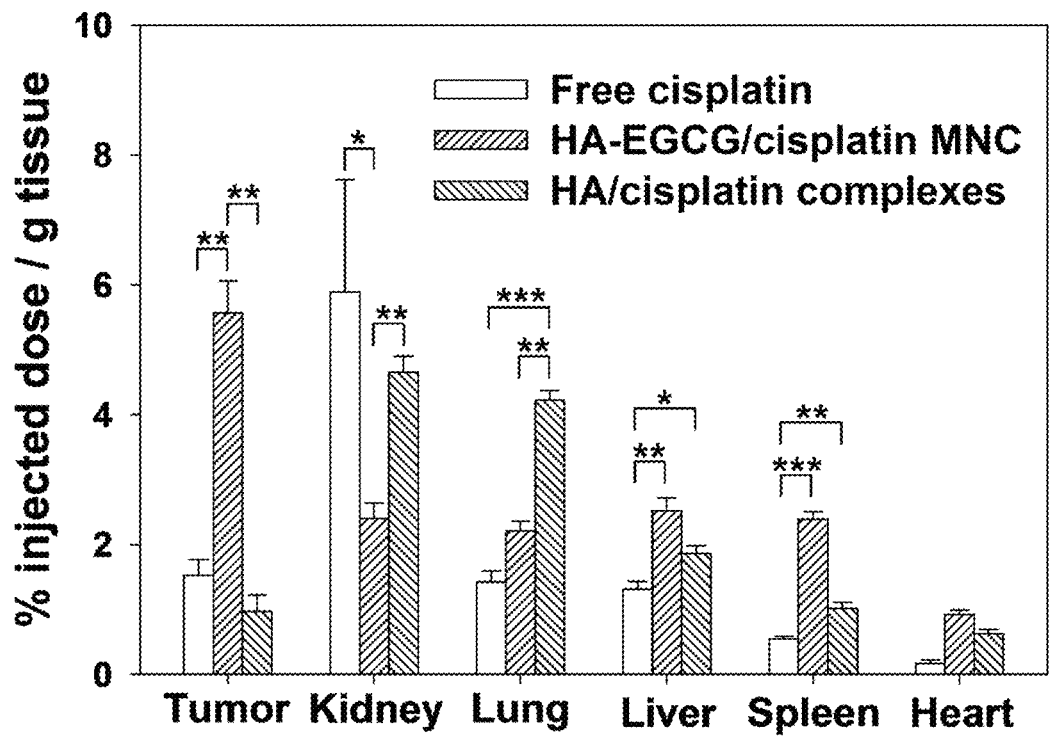

[Fig. 11]
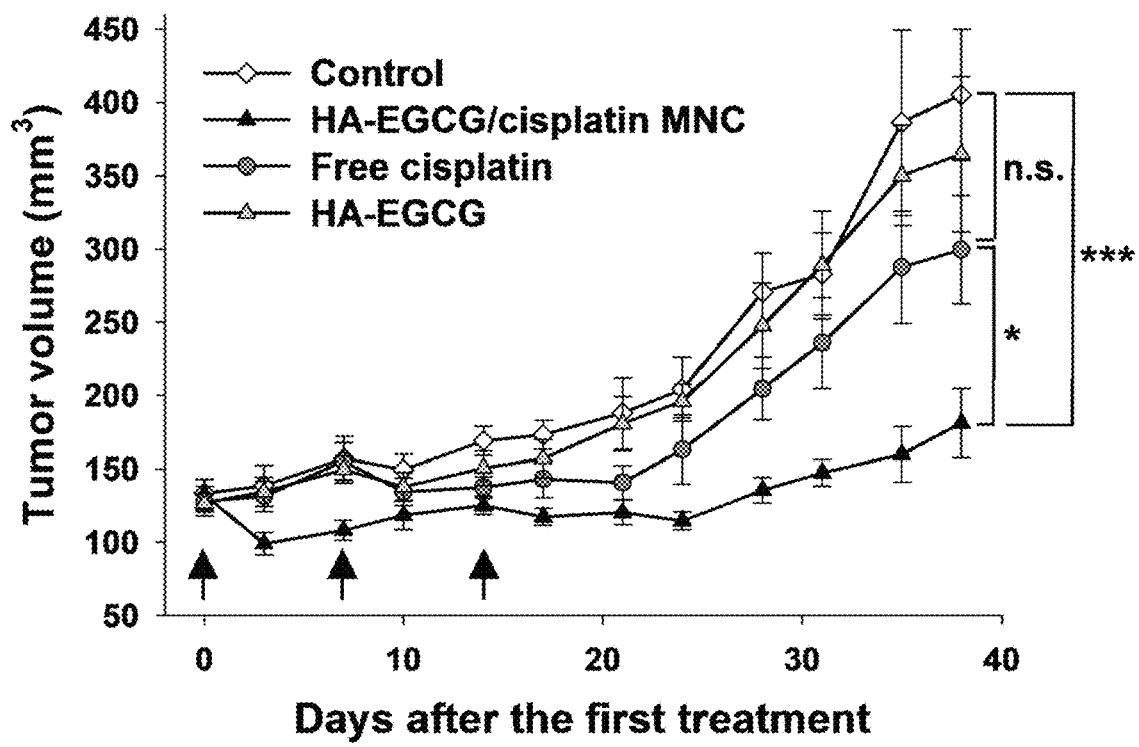
[Fig. 12]
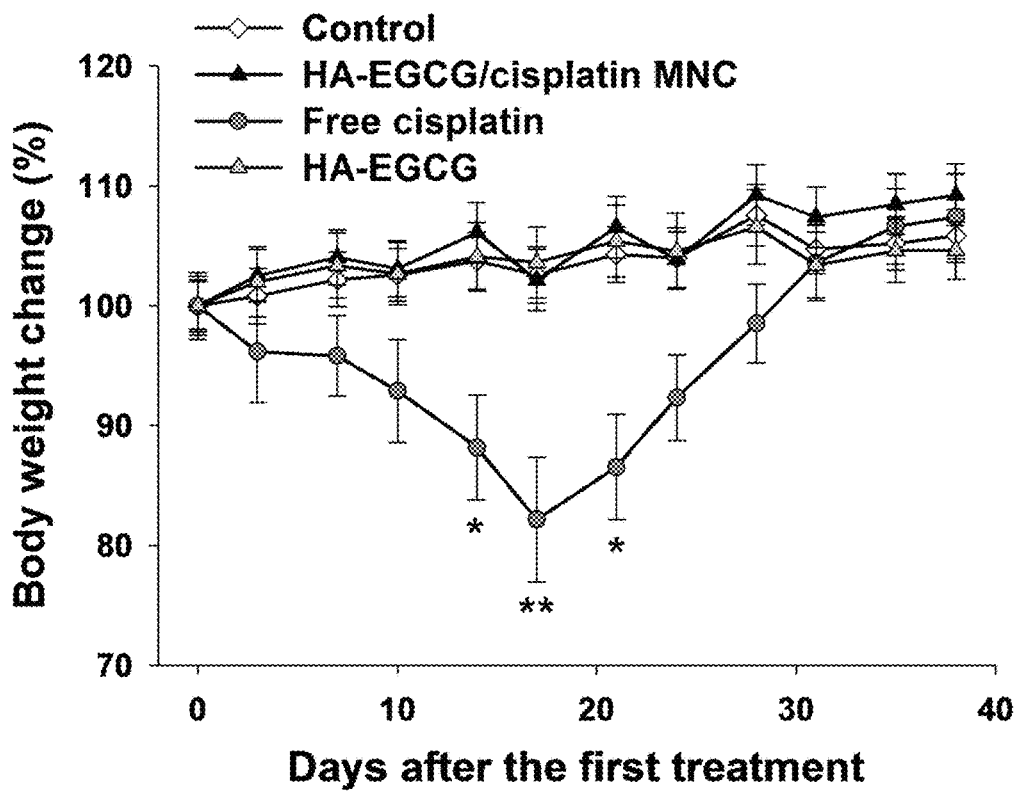

[Fig. 13A]
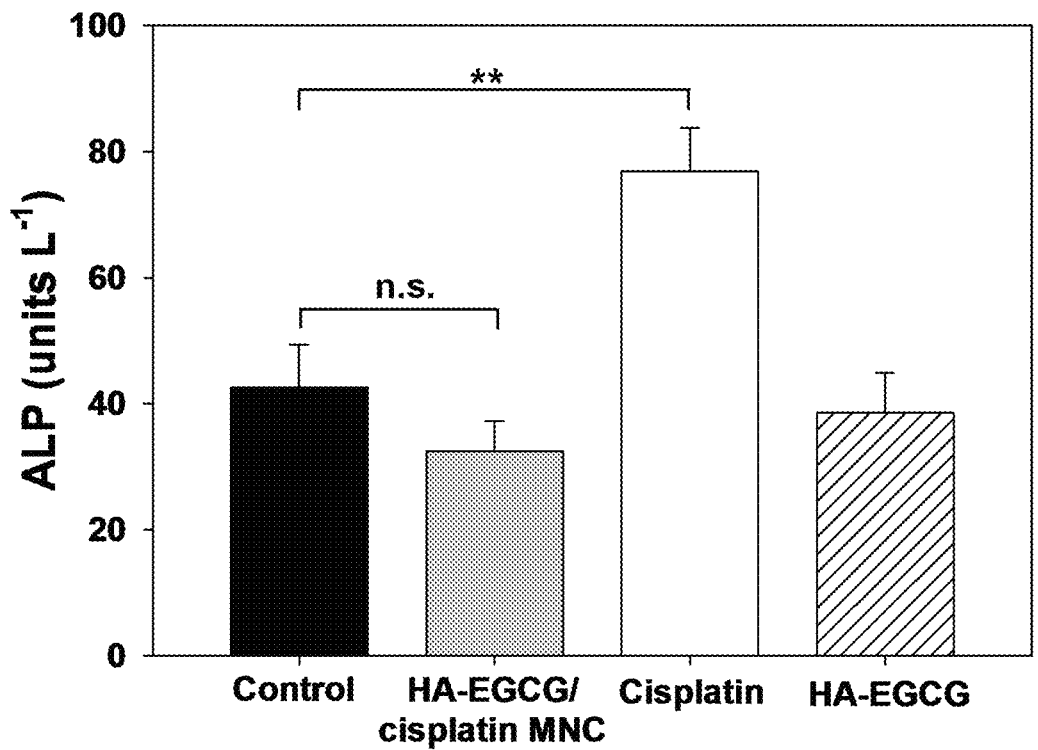
[Fig. 13B]
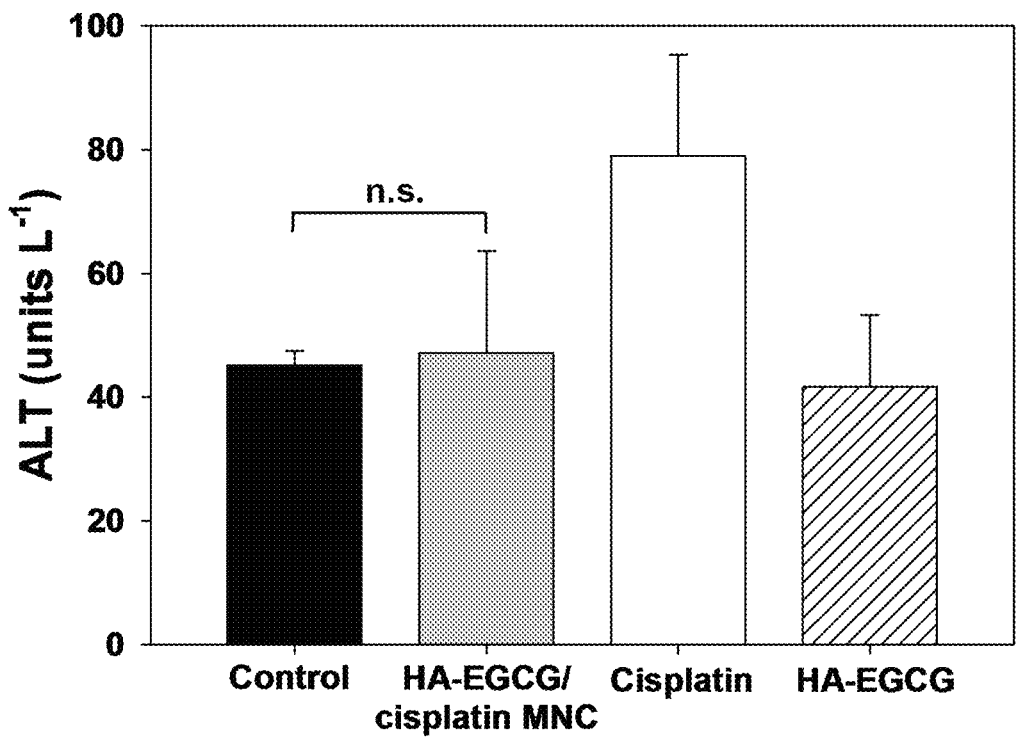

[Fig. 13C]
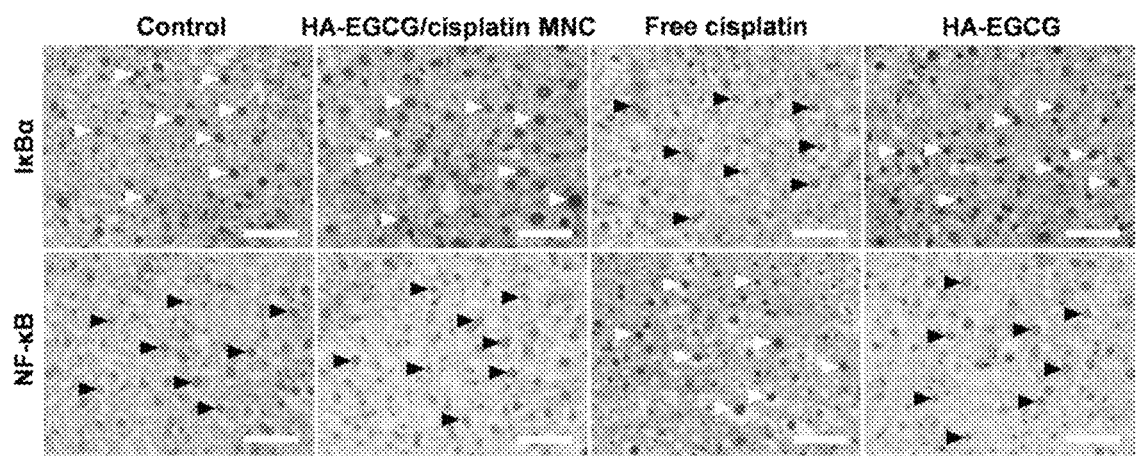
[Fig. 13D]
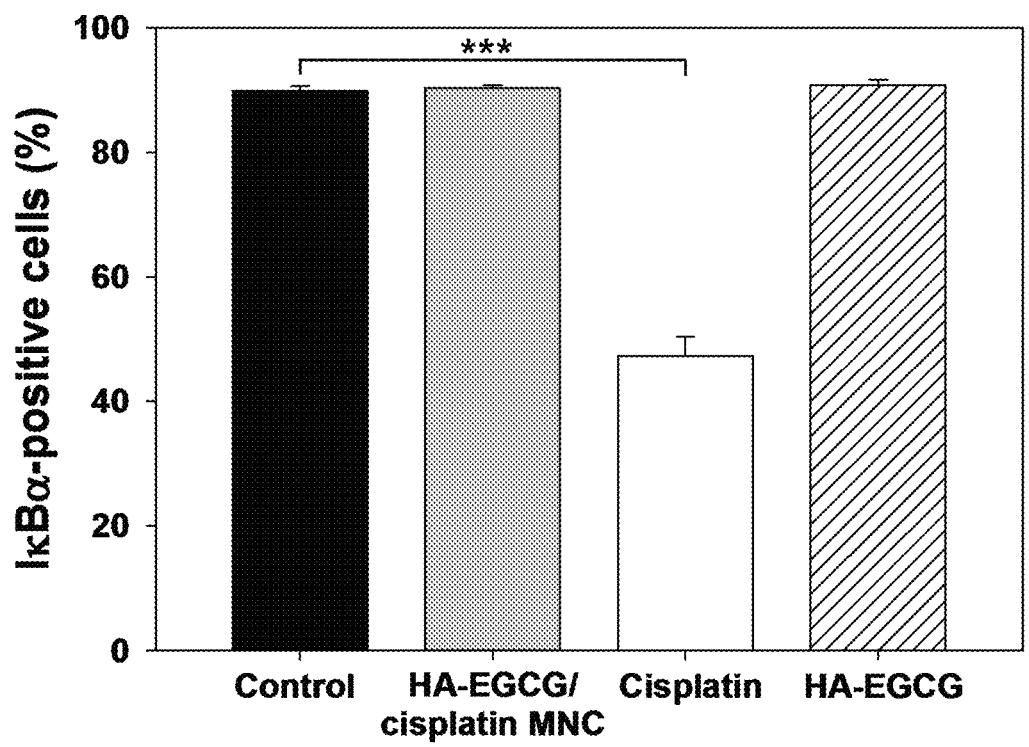

[Fig. 13E]
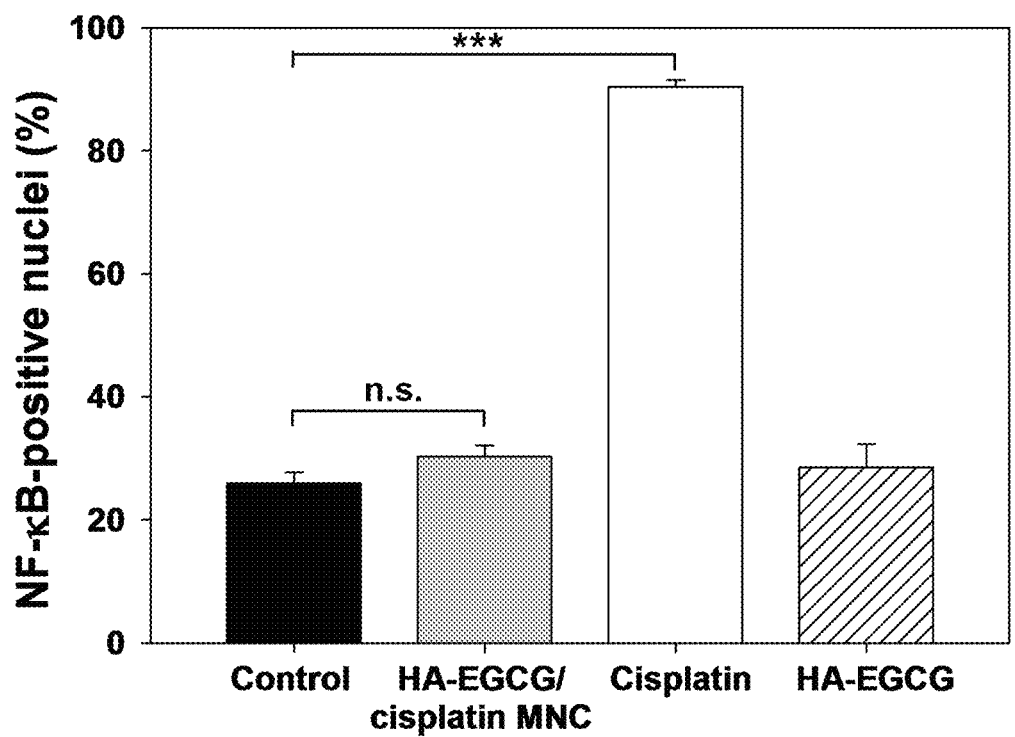

[Fig. 14A]
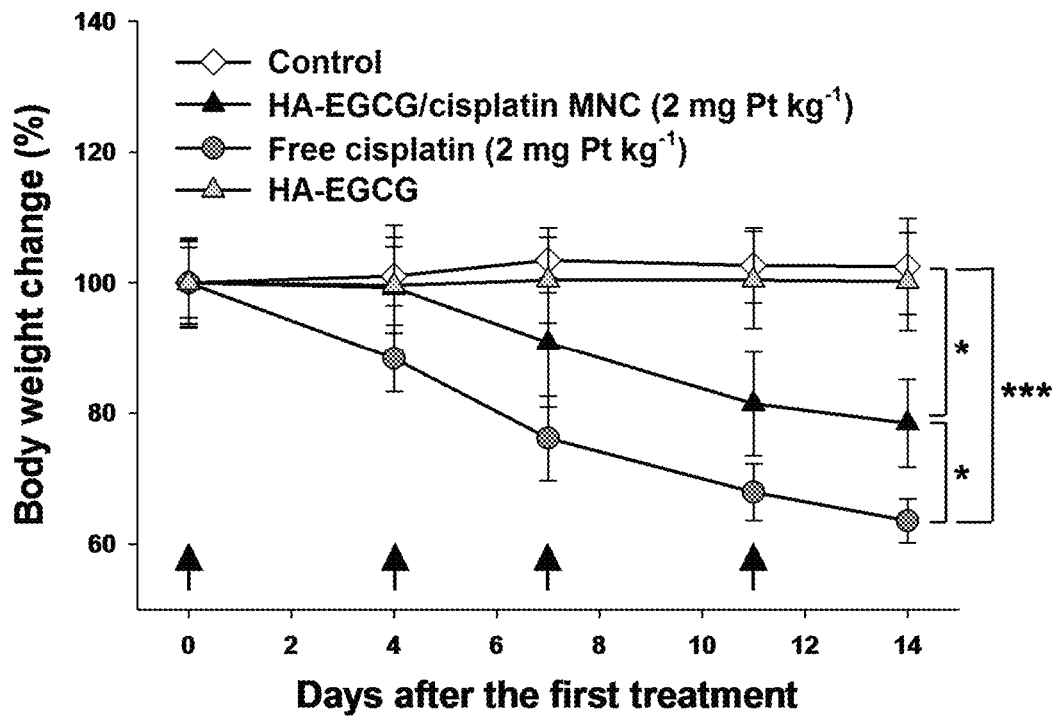
[Fig. 14B]
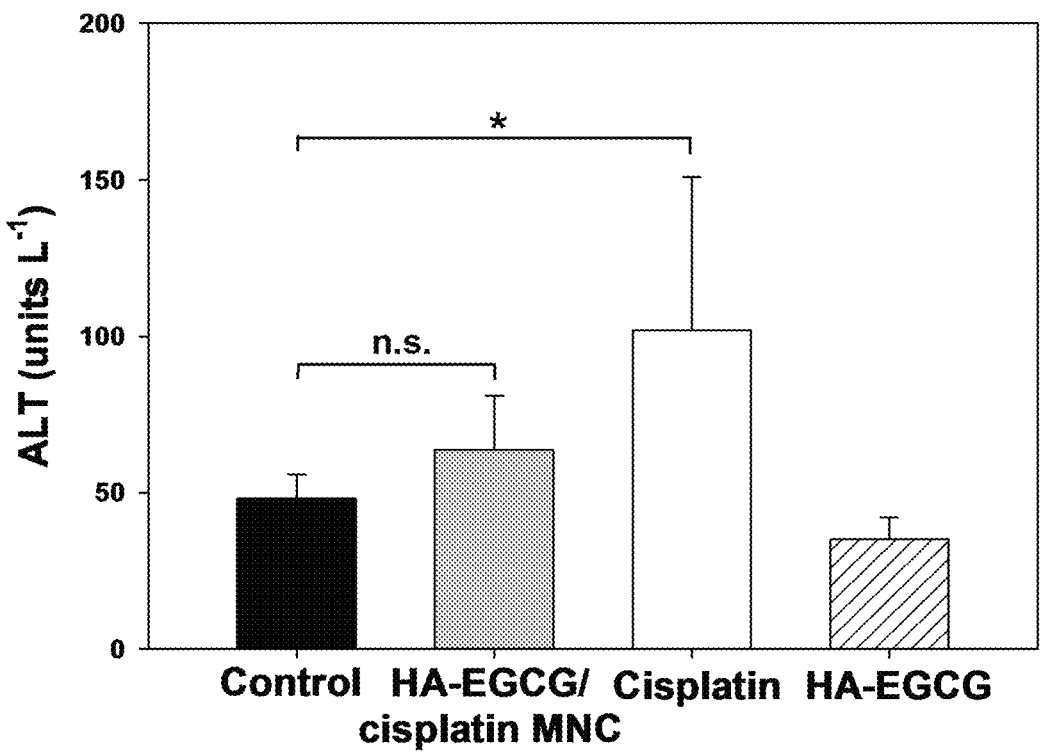

[Fig. 14C]
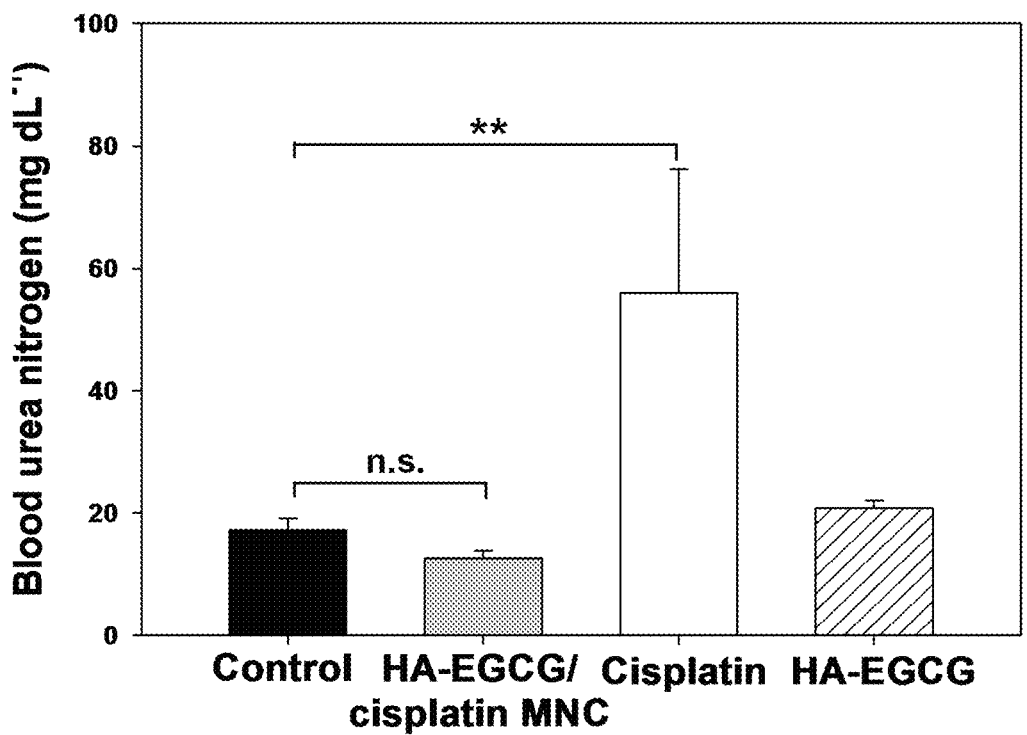
[Fig. 14D]
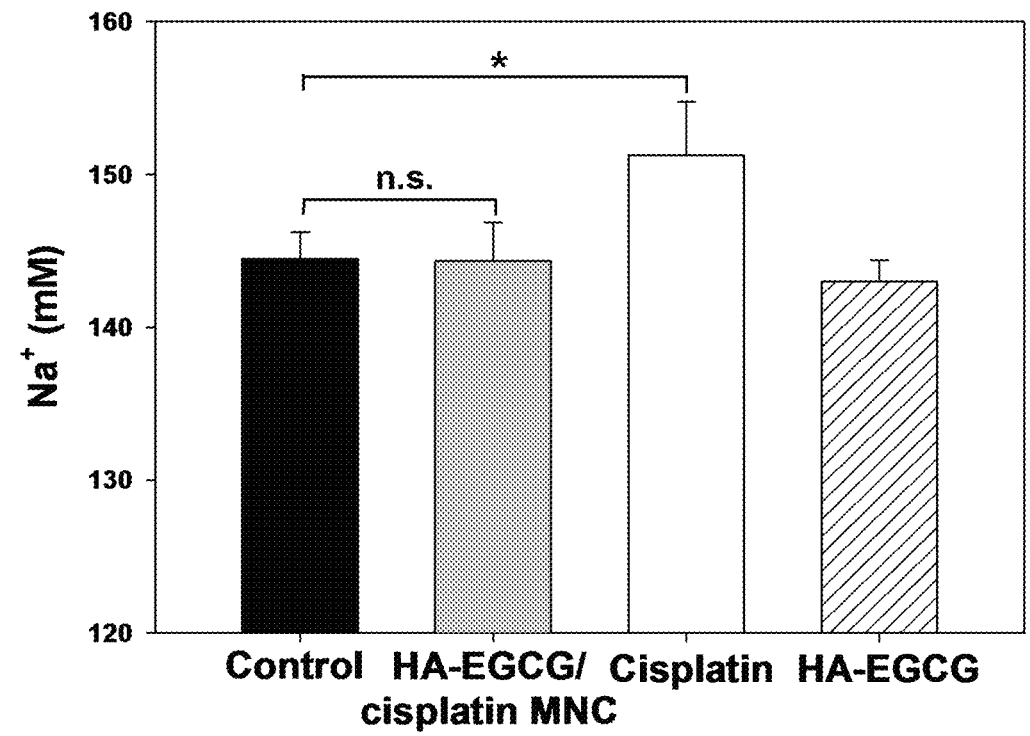

[Fig. 15]
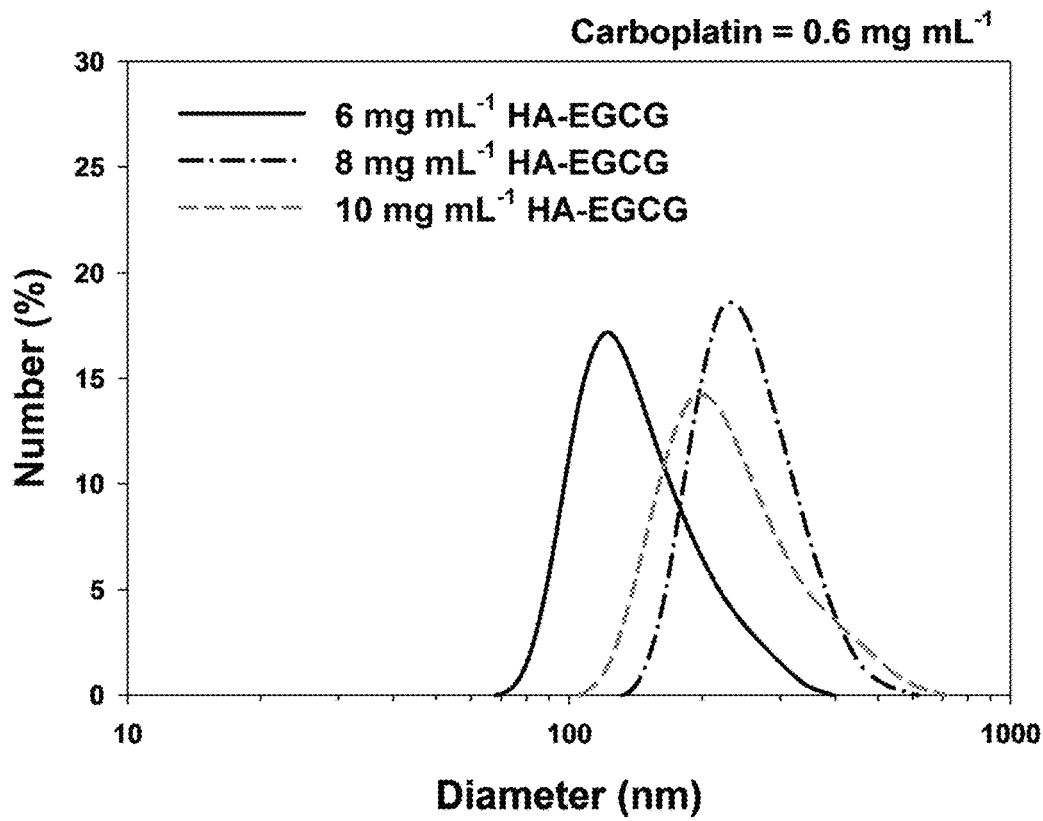
[Fig. 16]
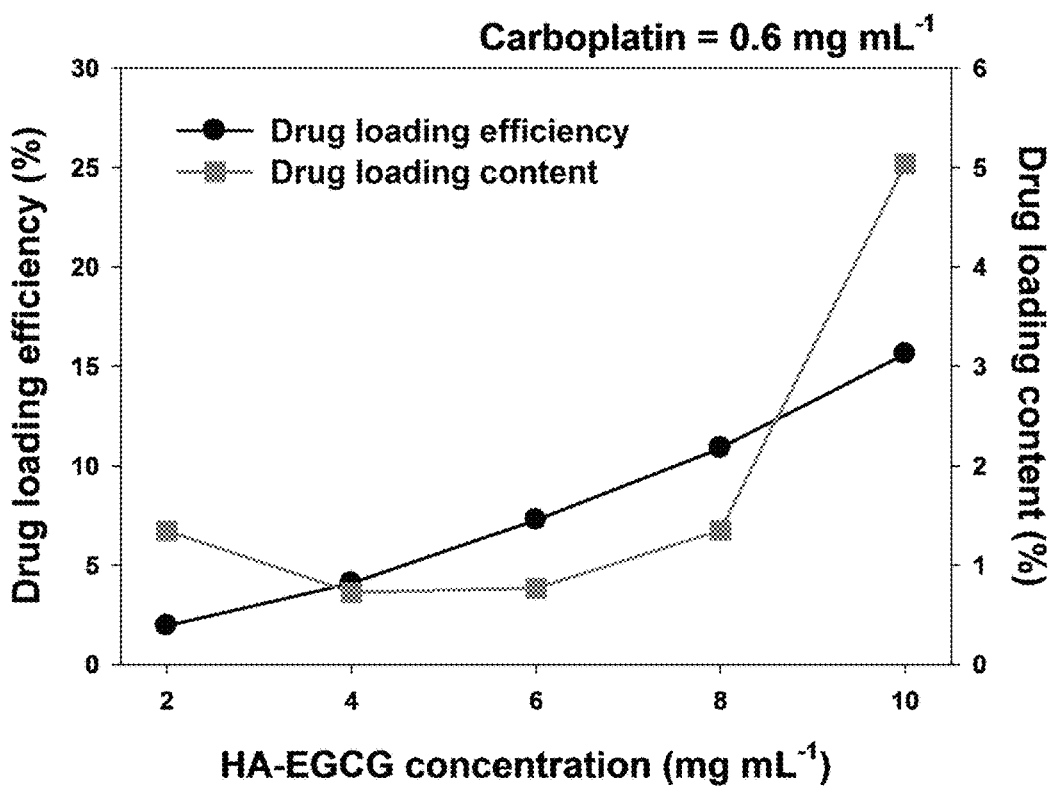

[Fig. 17]
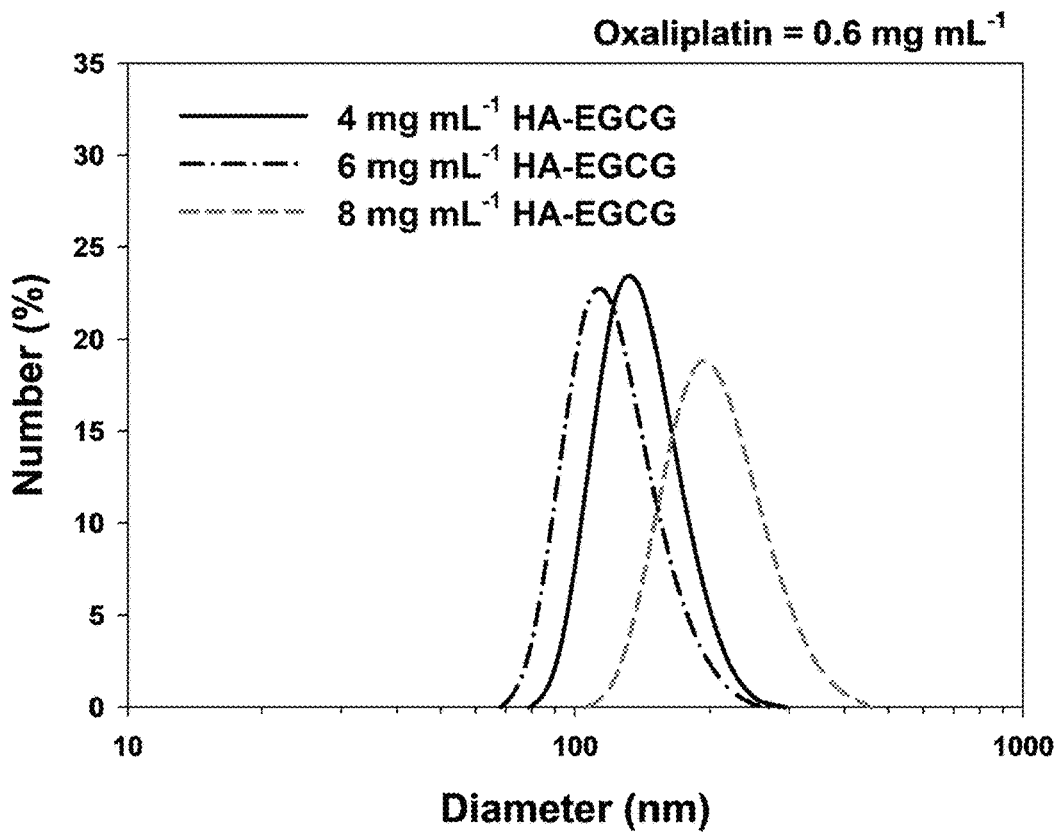
[Fig. 18]
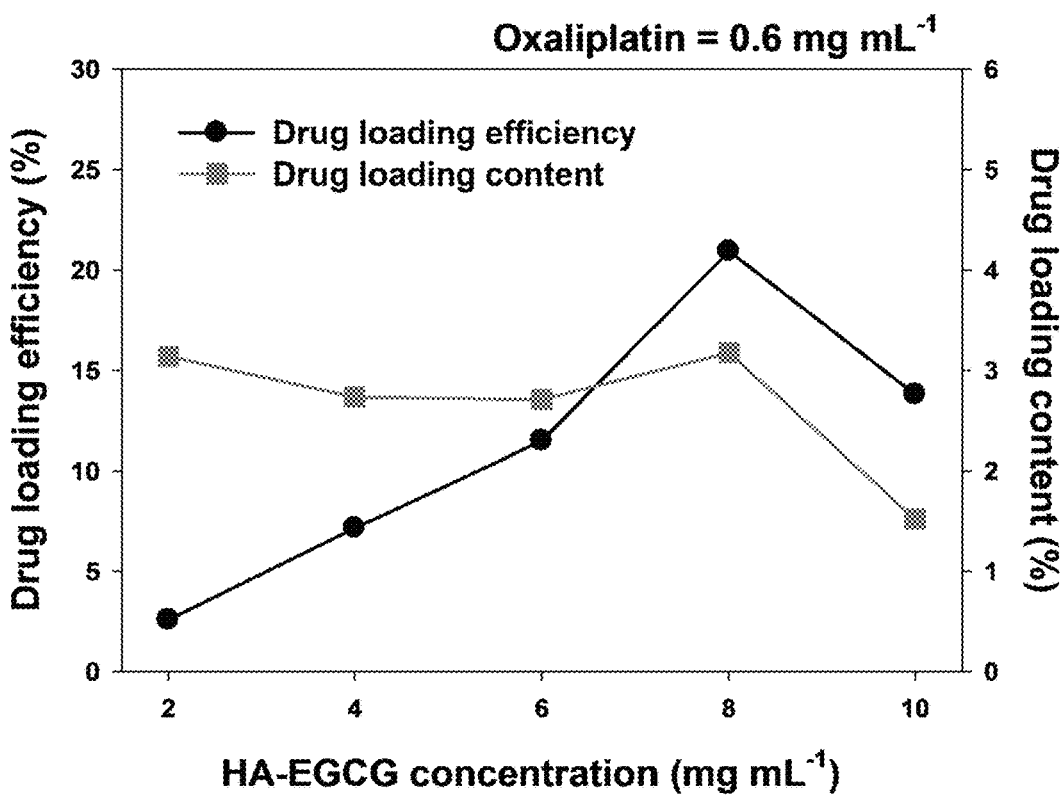

[Fig. 19]
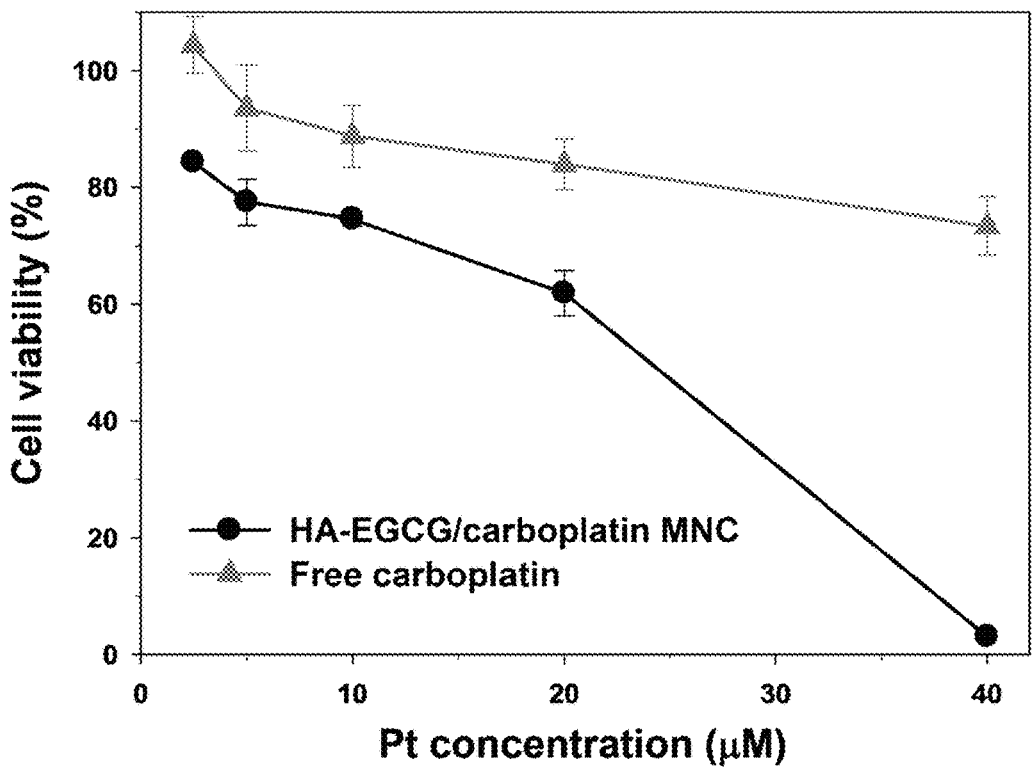
[Fig. 20]
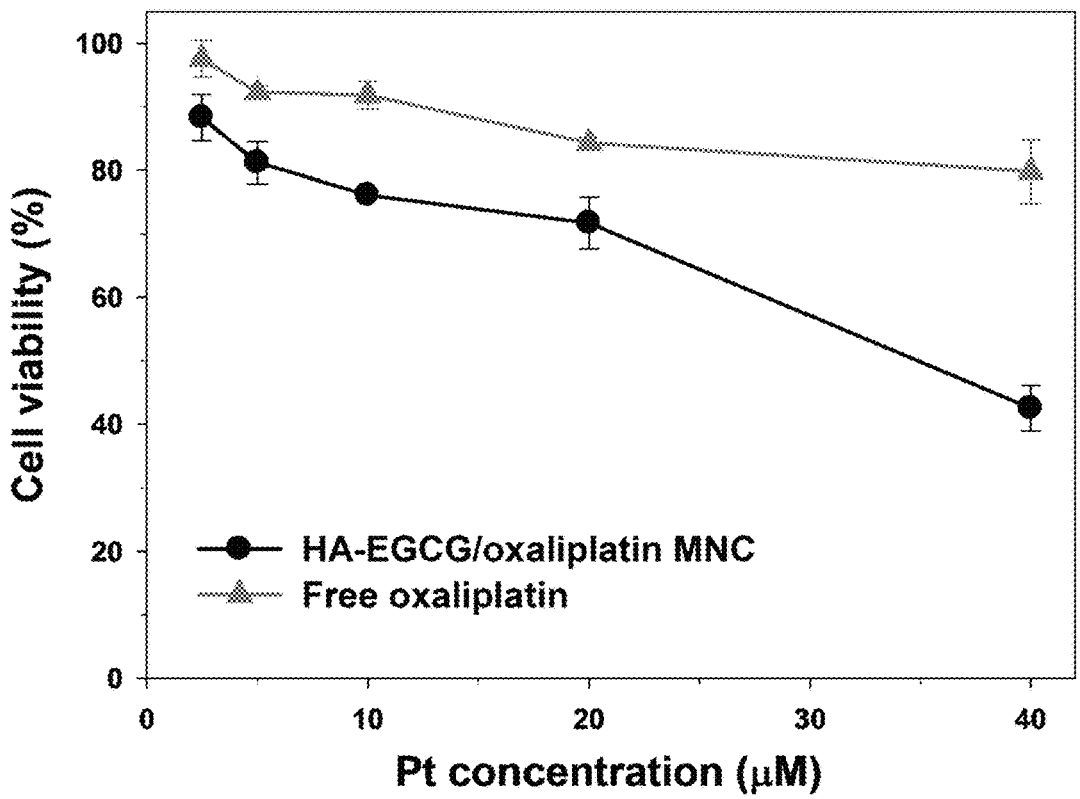

NANOCOMPLEX

RELATED APPLICATION

This application claims priority to Singapore patent application number 10201610979T, the disclosure of which is hereby incorporated herein by reference.

TECHNICAL FIELD

The present invention generally relates to a nanocomplex having a core-shell structure. The present invention also relates to a method for forming the nanocomplex and uses of the nanocomplex.

BACKGROUND ART

Anticancer drugs such as those containing platinum have been popularly used in the treatment of a broad range of cancers including ovarian, cervical, testicular, bladder and non-small cell lung cancers. Currently, it is estimated that as many as 50 to 70% of cancer patients are treated with platinum-based anticancer drugs. However, a number of patients receiving such treatment experience serious side effects such as nephrotoxicity, neurotoxicity and ototoxicity, which may result from non-specific systemic distribution of the anticancer drugs.

Over the past decades, there have been considerable efforts to develop delivery systems for such anticancer drugs, where the delivery systems are able to provide superior antitumor efficacy and reduced toxicity. For example, existing delivery systems for cisplatin include liposomal cisplatin, N-(2-hydroxypropyl)methacrylamide copolymer-cisplatin conjugates or poly(ethylene glycol)-poly(glutamic acid) block copolymer micelles, where these are used as nanocarriers for cisplatin delivery. Such nanocarriers are designed to increase the intratumoral concentration of cisplatin by accumulating in tumors preferentially via the enhanced permeability and retention effect, a phenomenon whereby nanoparticles tend to extravasate through the leaky tumor vasculature and accumulate within the tumor due to an impaired lymphatic drainage. While only a few cisplatin nanocarriers have entered clinical investigation, the results of such cisplatin nanocarriers were not satisfactory. In a Phase I clinical trial of cisplatin-loaded block copolymer micelles, hypersensitivity reactions occurred more frequently than those caused by cisplatin although disease stabilization was observed in 7 out of 17 patients with advanced solid tumors. A randomized Phase III study of liposomal cisplatin plus paclitaxel demonstrated a reduction of cisplatin-related toxicity compared to the combination of cisplatin with paclitaxel, but there was no significant improvement in the effectiveness in patients with inoperable (stage IIIb/IV) non-small-cell lung cancer. Hence, alleviation of off-target toxicity of cisplatin still remains a challenge because the majority of systemically administered nanoparticles are sequestered by the mononuclear phagocytic system distributed in healthy organs and tissues.

There is a need to provide a nanocomplex that overcomes, or at least ameliorates, one or more of the disadvantages described above.

There is a need to provide the nanocomplex as a delivery system that is able to have reduced toxicity, better stability and/or slower clearance from a patient as compared to known delivery systems.

SUMMARY

According to a first aspect, there is provided a nanocomplex having a core-shell structure, the shell comprising a functionalized hyaluronic acid and the core comprising a flavonoid encapsulating a metal-containing compound.

The functionalized hyaluronic acid and the flavonoid form a conjugate. A plurality of the conjugates may form a micelle where the plurality of functionalized hyaluronic acids form the "tail" portion of the micelle and the plurality of flavonoids form the "head" portion of the micelle. Here, the hydrophobic flavonoids "head" is at the center of the micelle and the hydrophilic functionalized hyaluronic acids "tail" form the outer region of the micelle. Where the conjugate encapsulates a metal-containing compound or metal-containing compounds, this forms a "nanocomplex" where the metal-containing compound(s) is encapsulated by the flavonoids "head" to form the core of the nanocomplex. The shell of the nanocomplex is then the outer region of the micelle. The nanocomplex can act as a delivery system to deliver the metal-containing compound(s) to a desired site (such as a tumour). This delivery can occur in an in vitro or in vivo manner.

The nanocomplex may have a smaller particle size than the conjugate. It is unexpected that the nanocomplex decreases in size as compared to the conjugate (that does not have the encapsulated metal-containing compound(s)) as one would expect the nanocomplex to be bigger than the conjugate due to the presence of the metal-containing compound(s) which would typically cause a bulging of the nanocomplex. This is seen in a known micellar encapsulation system made up of a copolymer of crosslinked poly (oligo(ethylene glycol) methyl ether methacrylate)-block-poly(styrene-co-3-isopropenyl-R,R-dimethylbenzyl isocyanate) loaded with a platinum based drug that increased in size upon cross-linking and loading of the drug into the micelle. However, this is not the case here and the nanocomplex unexpectedly decreases in size after encapsulation of the metal-containing compound(s). The smaller particle size of the nanocomplex may surprisingly allow for longer blood circulation when administered to a patient, leading to slower clearance from the patient. This advantageously allows for longer treatment period and possibly lesser dosing frequency, leading to better patient compliance.

Advantageously, the nanocomplex may have higher loading and loading efficiency of the metal-containing compound(s) as compared to known delivery systems or when compared to a complex of (unmodified) hyaluronic acid with the metal-containing compound(s).

Advantageously, the nanocomplex may be more stable physiologically as compared to known delivery systems or when compared to a complex of (unmodified) hyaluronic acid with the metal-containing compound(s). This may aid in increasing the accumulation of the nanocomplex in tumours via the enhanced permeability and retention effect.

Advantageously, the nanocomplex may be able to selectively target a desired type of tumour, such as a tumour that produces hyaluronidase, a CD-44 overexpressing primary or a CD44-overexpressing metastatic tumour, as compared to known delivery systems or when compared to a complex of (unmodified) hyaluronic acid with the metal-containing compound(s). By being able to selectively target a desired type of tumour, the nanocomplex is able to deliver the metal-containing compound (the anticancer drug) effectively to that tumour, leading to treatment of that tumour. Without the selective targeting ability of the nanocomplex, this may lead to delivery of the metal-containing compound to undesired cells of the patient, including normal cells, leading to severe side effects due to the toxicity of the metal-containing compound.

According to a second aspect, there is provided a method for forming a nanocomplex having a functionalized hyaluronic acid shell and a core comprising a flavonoid encapsulating a metal-containing compound, the method comprising the step of mixing a solution of the metal-containing compound with a solution of a conjugate of the functionalized hyaluronic acid and the flavonoid.

According to a third aspect, there is provided a pharmaceutical composition comprising a nanocomplex having a core-shell structure and a pharmaceutically acceptable carrier or excipient, wherein the shell comprises a functionalized hyaluronic acid and the core comprises a flavonoid encapsulating a metal-containing compound.

According to a fourth aspect, there is provided a nanocomplex having a core-shell structure for use as a medicament, wherein the shell comprises a functionalized hyaluronic acid and the core comprises a flavonoid encapsulating a metal-containing compound.

According to a fifth aspect, there is provided use of a nanocomplex having a core-shell structure in the manufacture of a medicament for the treatment of cancer, wherein the shell comprises a functionalized hyaluronic acid and the core comprises a flavonoid encapsulating a metal-containing compound.

According to a sixth aspect, there is provided a method of treating cancer comprising administering a nanocomplex having a core-shell structure to a cancer patient, wherein the shell comprises a functionalized hyaluronic acid and the core comprises a flavonoid encapsulating a metal-containing compound.

DEFINITIONS

The following words and terms used herein shall have the meaning indicated:

The term 'flavonoid' is to be interpreted broadly to refer to a broad class of plant secondary metabolites including without limitation the typical flavonoids (also named bioflavonoids), isoflavonoids, derived from a 3-phenyl-chromen-4-one (3-phenyl-1,4-benzopyrone) structure, neoflavonoids, derived from a 4-phenylcoumarine (4-phenyl-1,2-benzopyrone) structure and similar polyphenolic compounds, or as defined below, as well as mixtures thereof. The flavonoid may have a core phenylbenzyl pyrone structure. A simplified depiction of the A, B and C rings of the flavonoid is shown below:

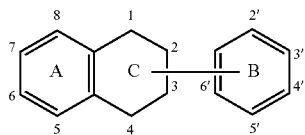

The term 'conjugate' is to be interpreted broadly to include a moiety formed by the union of two compounds or a moiety united with another moiety. According to the disclosure, the conjugation is by a covalent chemical bond.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a nanocomplex will now be disclosed.

The nanocomplex has a core-shell structure, where the shell comprises a functionalized hyaluronic acid and the core comprises a flavonoid encapsulating a metal-containing compound.

As mentioned above, the functionalized hyaluronic acid and the flavonoid form a conjugate. A plurality of the conjugates may form a micelle where the plurality of functionalized hyaluronic acids form the "tail" portion of the micelle and the plurality of flavonoids form the "head" portion of the micelle. Where the conjugate encapsulates a metal-containing compound or metal-containing compounds, forming a nanocomplex, the metal-containing compound(s) is encapsulated by the flavonoids "head" to form the core of the nanocomplex, while the shell of the nanocomplex is the outer region of the micelle.

The nanocomplex may have a particle size that is smaller than the particle size of the conjugate comprising the functionalized hyaluronic acid and the flavonoid. The particle size of the nanocomplex may be about 10% to about 70%, about 10% to about 20%, about 10% to about 30%, about 10% to about 40%, about 10% to about 50%, about 10% to about 60%, about 20% to about 70%, about 30% to about 70%, about 40% to about 70%, about 50% to about 70%, or about 60% to about 70%, of the particle size of the conjugate, where the particle size of the conjugate is determined based on the particle size of the conjugate when formed as a micelle. As an example, if the particle size of the conjugate micelle is about 100 nm, then the particle size of the nanocomplex (made up of the conjugate with the encapsulated metal-containing compound(es) is in the range of about 10 nm to about 70 nm.

The particle size of the nanocomplex thus depends on the particle size of the conjugate micelle where the particle size of the nanocomplex is smaller than the conjugate micelle. As a guideline, the particle size of the nanocomplex may be in the range of about 30 nm to about 150 nm, about 30 nm to about 40 nm, about 30 nm to about 50 nm, about 30 nm to about 60 nm, about 30 nm to about 70 nm, about 30 nm to about 80 nm, about 30 nm to about 90 nm, about 30 nm to about 100 nm, about 30 nm to about 110 nm, about 30 nm to about 120 nm, about 30 nm to about 130 nm, about 30 nm to about 140 nm, about 40 nm to about 150 nm, about 50 nm to about 150 nm, about 60 nm to about 150 nm, about 70 nm to about 150 nm, about 80 nm to about 150 nm, about 90 nm to about 150 nm, about 100 nm to about 150 nm, about 110 nm to about 150 nm, about 120 nm to about 150 nm, about 130 nm to about 150 nm, about 140 nm to about 150 nm, or about 50 nm to about 70 nm. The particle size may be of any discrete or individual value that is within any of the above range or sub-range, to the appropriate number of decimal point(s).

The particle size of the nanocomplex or the conjugate micelle refers to the diameter (or equivalent spherical diameter if the nanocomplex or conjugate micelle is not spherical). The diameter may be an average diameter taken from a number of measurements of the same nanocomplex or the same conjugate micelle, or the average diameter of a number of nanocomplexes or conjugate micelles. The diameter may be a hydrodynamic diameter that may be obtained by using a particle size analyser. As an example only, the particle size analyser may be a Zetasizer Nano ZS device from Malvern Instruments from the United Kingdom. Other particle size analysers that are able to measure to the nano scale can also be used.

The functionalized hyaluronic acid may be a thiol-functionalized hyaluronic acid.

The functionalized hyaluronic acid may have a molecular weight in the range of about 1 kDa to about 50 kDa.

The presence of the hyaluronic acid may aid in the selective targeting of the nanocomplex to a desired type tumour. The hyaluronic acid may facilitate the degradation of the nanocomplex when at the desired tumour site. Where the tumour is one that produces hyaluronidase, the hyaluronidase present at the tumour degrades the hyaluronic acid, leading to the destabilization or dissociation of the noncomplex and the release of the metal-containing compound(es) from the nanocomplex to the tumour. The accelerated release of the metal-containing compound enables rapid localization of the metal-containing compound to the nucleus of a cell and thus promote the formation of adducts of the metal-containing compound with DNA, which interfere with DNA replication and transcription, leading to the enhanced killing of the tumour cells. This may aid in ensuring that the release of the metal-containing compound(es) happens at the desired tumour site, thus ensuring that other types of cells are protected from the metal-containing compound(es). This may also aid in minimizing premature leakage of the metal-containing compound(es) during systemic circulation.

The desired tumour may be a CD44-overexpressing primary, a CD44-overexpressing metastatic tumor, or a hyaluronidase expressing tumor.

The hyaluronic acid present in the nanocomplex may interact with the CD44 on the CD44-overexpressing tumour to aid in the internalization of the nanocomplex (via hyaluronic acid-CD44 interactions) into the CD44-overexpressing cancer cells or tumour. Once internalized, the nanocomplex is able to deliver the metal-containing compound(s) to the desired tumour (or cancer cells). Thus, in this manner, the noncomplex is able to selectively target a desired tumour, such as a CD44-overexpressing tumour.

The flavonoid may be selected from the group consisting of isoflavonoids, neoflavonoids, flavonols, flavones, isoflavones, flavanoids, flavanols, flavans, tannins, oolongtheanin, theacitrin, theaflavins and theasinensin.

The flavonoid may be selected from the group consisting of epicatechin gallate, epigallocatechin, Gallocatechin, Gallocatechin gallate, Robinetinidol, ellagitannin, gallotannin, oolongtheanin, tannin, theacitrin, theasinensin and mixtures thereof.

If not specifically-mentioned, the application includes within its scope all isomeric forms of the compounds disclosed herein, including all diastereomeric isomers, racemates and enantiomers. Thus, flavonoids should be understood to include, for example, E, Z, cis, trans, (R), (S), (L), (D), (+) and/or (−) forms of the compounds, as appropriate in each case, if not specifically mentioned otherwise.

The flavonoid may be the terminal group of the conjugate or the flavonoid may be grafted onto the functionalized hyaluronic acid.

The flavonoid may aid in enhancing the anticancer efficacy of the metal-containing compound by increasing the sensitivity of the cancer cells to the metal-containing compound. In addition, the flavonoid may have antioxidant, free radical scavenging and/or anti-inflammatory properties that may aid in reducing the toxicity of the metal-containing compound. The antioxidant activity of the flavonoid may avoid off-target toxicity in healthy organs by minimizing oxidative stress that is evoked by the metal-containing compound.

The presence of the functional group on the functionalized hyaluronic acid may act as a linker to conjugate the hyaluronic acid to the flavonoid. Thus, the functional group may be a thiol functional group. The conjugation of the functionalized hyaluronic acid to the flavonoid may be via covalent bonding.

The functionalized hyaluronic acid may be conjugated to at least one flavonoid, or at least two flavonoids. The functionalized hyaluronic acid may be conjugated to two flavonoids, each independently selected from the group consisting of isoflavonoids, neoflavonoids, flavonols, flavones, isoflavones, flavanoids, flavanols, flavans, tannins, oolongtheanin, theacitrin, theaflavins and theasinensin. Where two flavonoids are conjugated, the two flavonoids may be the same or may be different from each other. One of the two flavonoids may be conjugated to the functionalized hyaluronic acid or both of two flavonoids may be conjugated to the functionalized hyaluronic acid.

The functionalized hyaluronic acid may be conjugated to the B ring or D ring of the flavonoid. Depending on the type of conjugation to the desired ring of the flavonoid, the type of functional group on the functionalized hyaluronic acid may be selected accordingly. Where required, if a corresponding functional group is required on the flavonoid for the conjugation, this would be known to a person skilled in the art. Hence, the flavonoid may optionally be functionalised or be modified with a functional group. For example, if B ring conjugation is desired, the functional group on the hyaluronic acid may be a thiol group.

The flavonoid may be epigallocatechin gallate (EGCG), having the structure below:

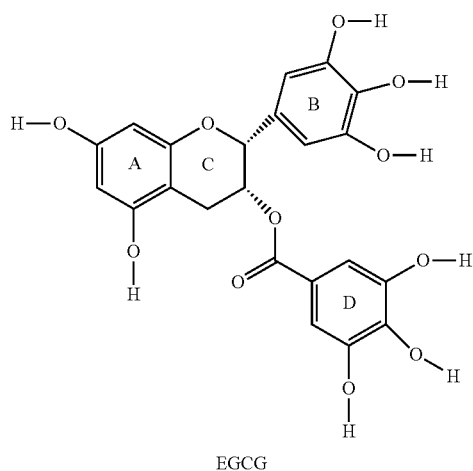

EGCG

The metal-containing compound may comprise a metal such as a transition metal. The transition metal as a transition metal ion may form stable coordination bonds with the flavonoid. The transition metal may be selected from the group consisting of platinum, ruthenium, iron, titanium and gallium. The metal-containing compound may be an anti-cancer drug. The metal-containing compound may be selected from the group consisting of cisplatin, carboplatin, oxaliplatin, dichloro(1,2-diaminocyclohexane)platinum(II), nedaplatin, heptaplatin, lobaplatin, satraplatin, miriplatin, aroplatin, picoplatin, dicycloplatin, phosphaplatin, phenanthriplatin, ruthenium arene 1,3,5-triaza-7-phospha-adamantane, indazolium trans-[tetrachlorobis(1H-indazole) ruthenate(III)], imadozolium trans-[tetrachloro)dimethylsulfoxide)(imidazole)ruthenate(III)], ferrocifens, titanoene dichloride and tris(8-quinolinolato)gallium(III).

Where the metal-containing compound is a platinum-containing complex, the platinum-containing complex may be selected from the group consisting of cisplatin, carboplatin, oxaliplatin, dichloro(1,2-diaminocyclohexane)platinum(II), nedaplatin, heptaplatin, lobaplatin, satraplatin, miriplatin, aroplatin, picoplatin, dicycloplatin, phosphaplatin and phenanthriplatin.

The metal-containing compound may be an anti-cancer agent, such as having an anti-tumour effect, a cytotoxic effect, an apoptotic effect, an anti-mitotic effect, an anti-angiogenesis effect, or a metastasis inhibitory effect. The metal-containing compound may inhibit or reduce tumour cell growth, inhibit or reduce carcinogenesis, kill cancer or tumour cells, inhibit or reduce carcinogenic or tumorigenic properties of a cancer cell or a tumour cell. The metal-containing compound may be used as an adjunct therapy with chemotherapy as part of a treatment plan or regime for a patient.

The metal-containing compound may form coordination bonds and hydrogen bonds with the flavonoid. Thus, the flavonoid may interact with the metal-containing compound to thereby encapsulate the metal-containing compound within the core of the nanocomplex.

The nanocomplex may be loaded with 7 to 10 wt % of the metal-containing compound, where the wt % is calculated based on the weight of the nanocomplex.

The metal-containing compound may be protected from premature release by the shell. Hence, the metal-containing compound may only be released from the nancomplex when the nanocomplex is sequestered to a desired tumor site. The shell also serves to protect normal, healthy cells or non-targeted cells from the toxicity effect of the metal-containing compound. Due to the properties of the flavonoid as mentioned above, the flavonoid together with the metal-containing compound may have a synergistic anticancer effect.

The nanocomplex may be a conjugate of a thiol-functionalized hyaluronic acid with epigallocatechin gallate, where the conjugate encapsulates a metal-containing compound. Here, the metal-containing compound may be a platinum-containing complex. The platinum-containing complex may be cisplatin, carboplatin, oxaliplatin, dichloro(1,2-diaminocyclohexane)platinum(II), nedaplatin, heptaplatin, lobaplatin, satraplatin, miriplatin, aroplatin, picoplatin, dicycloplatin, phosphaplatin, or phenanthriplatin. Here, the nanocomplex may have a particle size in the range of about 30 nm to about 150 nm, or in the range of about 50 nm to about 70 nm. The particle size of the nanocomplex may be any individual value therebetween the above range or sub-range, to the appropriate decimal point(s).

The conjugate of the thiol-functionalized hyaluronic acid with epigallocatechin gallate may be of the following structure I or structure II:

Structure I

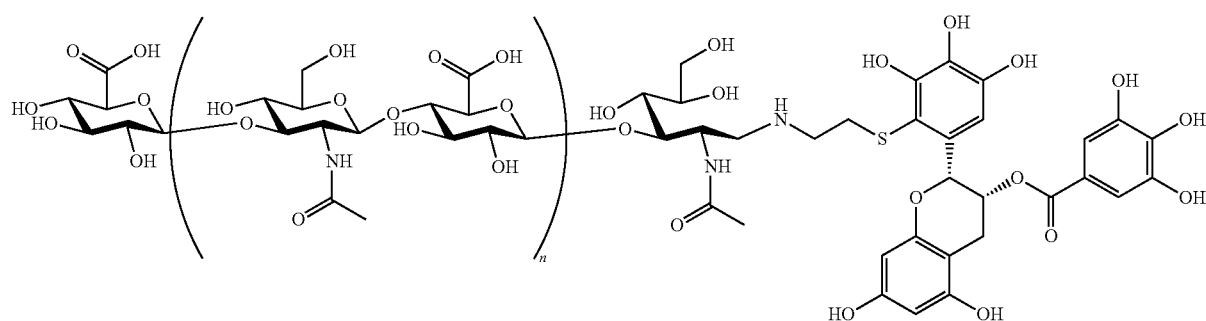

where n is independently an integer from 1 to 15,000 inclusive (or from 1 to 1,000, or from 1 to 100);

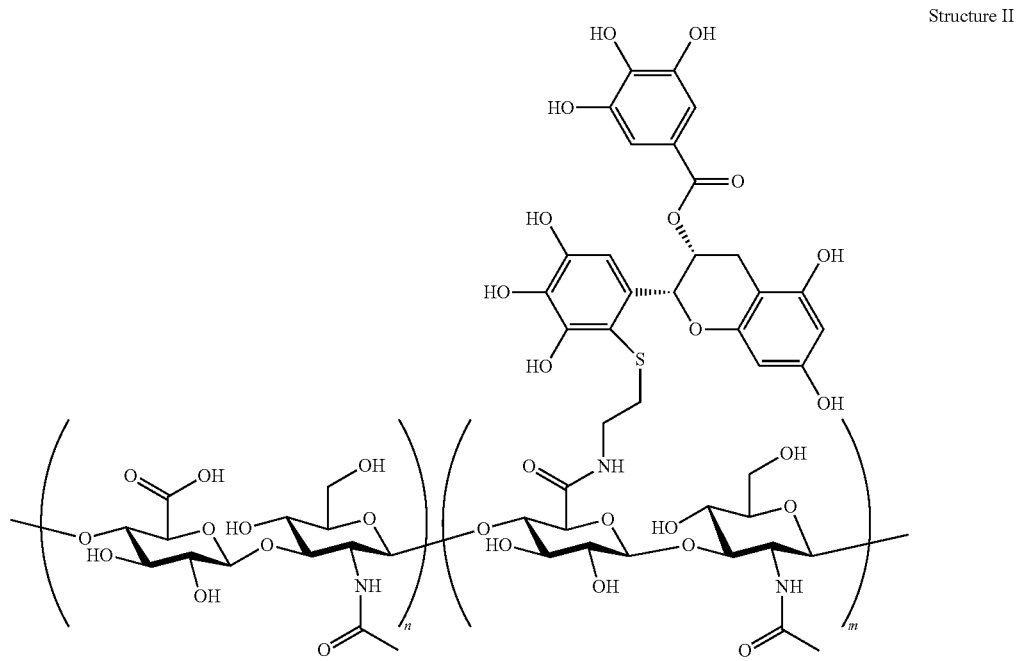

Structure II where each n is independently an integer from 0 to 15,000 (or from 0 to 1,000, or from 0 to 100) and each m is independently an integer from 1 to 15,000 (or from 1 to 1,000, or from 1 to 100).

Exemplary, non-limiting embodiments of a method for forming a nanocomplex will now be disclosed.

The method for forming the nanocomplex (where the nanocomplex has a functionalized hyaluronic acid shell and a core comprising a flavonoid encapsulating a metal-containing compound) comprises the step of mixing a solution of the metal-containing compound with a solution of a conjugate of the functionalized hyaluronic acid and the flavonoid.

The method may comprise a step of forming the functionalized hyaluronic acid. This may be carried out by modifying or functionalizing hyaluronic acid with a functional group. The functional group may be a thiol functional group.

The method may comprise a step of forming the conjugate of the functionalized hyaluronic acid and the flavonoid. This may involve the addition of a solution of the functionalized hyaluronic acid to a solution of the flavonoid and mixed. The solution used for both the functionalized hyaluronic acid and the flavonoid may be a saline buffer solution. The mixing of both solutions may be undertaken under basic condition (where pH is more than 7, such as between a pH of 7 to 8) and stirred for an appropriate time (such as for 5 to 10 hours) at an appropriate temperature (such as about 20° C. to about 30° C.). After this, the pH of the mixture was adjusted to acidic, such as less than 7, to stop the conjugation reaction. The resultant solution was then subject to dialysis to isolate the conjugate and to ensure that the conjugates are provided in an appropriate solvent for the next step.

The conjugate in solution is then mixed with the solution of the metal-containing compound. This may be undertaken for a period of time (such as about 24 hours to about 5 days, or about 3 days), at a particular temperature (such as about 30° C. to about 40° C., or about 37° C.), at a suitable stirring speed. The mixing step may be conducted in the absence of light. The time period taken may be about 24 hours, about 48 hours or about 72 hours. The temperature may be about 30° C., about 31° C., about 32° C., about 33° C., about 34° C., about 35° C., about 36° C., about 37° C., about 38° C., about 39° C., or about 40° C.

Once the conjugate is formed, the method may comprise the step of isolating the formed nanocomplex. This may be carried out via filtration or centrifugation or known isolation techniques.

The method may comprise the step of purifying the isolated nanocomplex. This may be carried out by dispersing the isolated nanocomplex in an aqueous solution (such as deionized water) and extracting the nanocomplex. This step may be repeated for a number of times.

The nanocomplex may be used as a delivery agent. The nanocomplex may be used to deliver the metal-containing compound to a desired tumour site within a subject or to cancer cells (where the delivery to the cancer cells can be done in vitro or in vivo). The nanocomplex may be administered parenterally (such as subcutaneously, intracutaneously, intravenously, intramuscularly, intraarticularly, intraarterially, intrasynovially, intrasternally, intrathecally, intralesionally, intracranial injection or by infusion techniques), by inhalation spray, topically, rectally, nasally, buccally, vaginally, via an implanted reservoir, by injection, subdermally, intraperitoneally, transmucosally, orally or in an ophthalmic preparation.

During intravenous administration, a suitable dosage was about 1 to about 7 mg of the drug/kg/week, about 1 to about 2 mg of the drug/kg/week, about 1 to about 3 mg of the drug/kg/week, about 1 to about 4 mg of the drug/kg/week, about 1 to about 5 mg of the drug/kg/week, about 1 to about 6 mg of the drug/kg/week, about 2 to about 7 mg of the drug/kg/week, about 3 to about 7 mg of the drug/kg/week, about 4 to about 7 mg of the drug/kg/week, about 5 to about 7 mg of the drug/kg/week, or about 6 to about 7 mg of the drug/kg/week.

A pharmaceutical composition comprising the nanocomplex having a core-shell structure and a pharmaceutically acceptable carrier or excipient may be provided, wherein the shell comprises a functionalized hyaluronic acid and the core comprises a flavonoid encapsulating a metal-containing compound. The pharmaceutical composition may further include additional therapeutic agents.

There is also provided a nanocomplex having a core-shell structure for use as a medicament, wherein the shell comprises a functionalized hyaluronic acid and the core comprises a flavonoid encapsulating a metal-containing compound.

There is also provided use of a nanocomplex having a core-shell structure in the manufacture of a medicament for the treatment of cancer or a tumour, wherein the shell comprises a functionalized hyaluronic acid and the core comprises a flavonoid encapsulating a metal-containing compound.

The cancer may be selected from the group consisting of testicular cancer, ovarian cancer, breast cancer, neck cancer, esophageal cancer, lung cancer, mesothelioma, neuroblastoma, uterine cancer, bladder cancer, cervical cancer, prostate cancer, liver cancer, nasopharyngeal cancer and brain cancer. The lung cancer may be non-small cell lung cancer.

There is provided a method of treating cancer or a tumour comprising administering a nanocomplex having a core-shell structure to a subject, wherein the shell comprises a functionalized hyaluronic acid and the core comprises a flavonoid encapsulating a metal-containing compound.

The cancer may be selected from consisting of testicular cancer, ovarian cancer, breast cancer, neck cancer, esophageal cancer, lung cancer, mesothelioma, neuroblastoma, uterine cancer, bladder cancer, cervical cancer, prostate cancer, liver cancer, nasopharyngeal cancer and brain cancer. The lung cancer may be non-small cell lung cancer.

The subject may be a mammal. The mammal may be a human. The human may be a cancer patient or a patient undergoing chemotherapy.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

Data are expressed as mean±standard deviation unless otherwise stated. Statistical comparisons were performed by one-way ANOVA with Tukey's multiple comparison test using the OriginPro 9 software (OriginLab Corporation, Northampton of Massachusetts of the United States of America). The Kaplan-Meier curves were analyzed by a log-rank test.

FIG. 1 is a schematic diagram showing a method to form an embodiment of the nanocomplex of the present application.

FIG. 2A-1 is a graph showing the hydrodynamic diameters of functionalized hyaluronic acid-epigallocatechin gallate/cisplatin micellar nanocomplexes (hereby termed as HA-EGCG/cisplatin MNCs), functionalized hyaluronic acid-epigallocatechin gallate (hereby termed as HA-EGCG) conjugate micelles, and hyaluronic acid/cisplatin (hereby termed as HA/cisplatin) complexes in deionized water. [FIG. 2A-2] is a graph showing the hydrodynamic diameters of poly(ethylene glycol)-epigallocatechin gallate conjugate micelles (hereby termed as PEG-EGCG) and poly(ethylene glycol)-epigallocatechin gallate/cisplatin micellar nanocomplexes (hereby termed as PEG-EGCG/cisplatin MNCs) in deionized water.

FIG. 2B to FIG. 2E are a number of transmission electron microscopy images showing the HA-EGCG/cisplatin MNCs (FIG. 2B at a scale of 100 nm, FIG. 2C at a scale of 30 nm) and HA/cisplatin complexes (FIG. 2D at a scale of 500 nm, FIG. 2E at a scale of 200 nm). The white arrows in FIG. 2C indicate the presence of HA shell layer.

FIG. 3A is a bar chart graph showing drug loading efficiency and loading content of HA/cisplatin complexes, HA-EGCG/cisplatin MNCs, and PEG-EGCG/cisplatin MNCs.

FIG. 3B-1 is a 3D bar chart showing the number-average diameter of HA-EGCG/cisplatin MNCs prepared from cisplatin and HA-EGCG at various final concentrations, while [FIG. 3B-2] is another 3D bar chart showing the drug loading content of HA-EGCG/cisplatin MNCs prepared from cisplatin and HA-EGCG at various final concentrations. Results are reported as mean values (n=3). HA-EGCG/cisplatin MNCs made from cisplatin (0.4 mg mL$^{-1}$) and HA-EGCG (4 mg mL$^{-1}$) were used in this study.

FIG. 4 is a graph showing the release profile of cisplatin from HA-EGCG/cisplatin MNCs and HA/cisplatin complexes in 10 mM phosphate-buffered saline (pH 7.4) at 37° C. For comparison, release of free cisplatin was evaluated under the same conditions.

FIG. 5 is a graph showing the release profile of HA-EGCG/cisplatin MNCs in 100 mM phosphate buffer (pH 6) containing various concentrations of hyaluronidase (HAase) at 37° C.

FIG. 6 is a bar chart graph showing platinum (Pt) content of SKOV-3, HCT116 and HEK293T cells treated for 24 h with HA-EGCG/cisplatin MNCs (80 μM Pt) in the presence or absence of free HA (10 mg mL=$^{1}$). Asterisks indicate a statistically significant difference between two groups; *P<0.05; n.s.: nonsignificant.

FIG. 7 is a bar chart graph showing viability of SKOV-3, HCT116 and HEK293T cells treated with HA-EGCG/cisplatin MNCs and HA/cisplatin complexes at a final platinum concentration of 80 μM. Asterisks indicate a statistically significant difference between two groups; *P<0.05; **P<0.01; n.s.: nonsignificant.

FIG. 8 is a bar chart graph showing caspase-3/7 expression levels of SKOV-3, HCT116 and HEK293T cells treated with HA-EGCG/cisplatin MNCs at various concentrations. Asterisks indicate a statistically significant difference between two groups; *P<0.05; **P<0.01.

FIG. 9 is a graph showing pharmacokinetic profiles of free cisplatin, HA-EGCG/cisplatin MNCs and HA/cisplatin complexes injected intravenously in SKOV-3 tumor-bearing mice. Results are presented as mean±SEM (n=4). Asterisks indicate a statistically significant difference between two groups; *P<0.05; **P<0.01.

FIG. 10 is a bar chart graph showing biodistribution profiles of free cisplatin, HA-EGCG/cisplatin MNCs and HA/cisplatin complexes at 4 hours post-injection. Results are presented as mean±SEM (n=4). Asterisks indicate a statistically significant difference between two groups; *P<0.05; P<0.01; *P<0.001.

FIG. 11 is a graph showing tumor growth of SKOV-3 tumor-bearing mice that received intravenous injection of free cisplatin (1 mg Pt kg$^{-1}$), HA-EGCG/cisplatin MNCs (1 mg Pt kg$^{-1}$) or HA-EGCG at an equivalent dose to that of MNCs (19.6 mg kg$^{-1}$). The black arrows indicate the time points of injection (days 0, 7, and 14). Results are presented as mean±SEM (n=10). Asterisks indicate a statistically significant difference between two groups; *P<0.05; ***P<0.001; n.s.: nonsignificant.

FIG. 12 is a graph showing body weight changes of SKOV-3 tumor-bearing mice that received intravenous injection of free cisplatin (1 mg Pt kg$^{-1}$), HA-EGCG/cisplatin MNCs (1 mg Pt kg$^{-1}$) or HA-EGCG at an equivalent dose to that of MNCs (19.6 mg kg$^{-1}$). Results are presented as mean±SEM (n=10). Asterisks indicate statistically significant differences between free cisplatin-treated and untreated control groups; *P<0.05; **P<0.01.

FIG. 13A is a bar chart graph showing the level of ALP in blood harvested at the 38-days endpoint.

FIG. 13B is a bar chart graph showing the level of ALT in blood harvested at the 38-days endpoint.

FIG. 13C is a number of images of histological sections of mouse livers after drug treatment. The images show cisplatin-mediated activation of NF-$_K$B signaling pathway.

FIG. 13D is a bar chart graph showing quantification of I$_K$Bα cells in the liver sections. The experiments were reproduced twice independently and representative images are shown. Results are presented as mean±SEM (n=10). Statistically significant differences between groups are marked as asterisks; ***P<0.001.

FIG. 13E is a bar chart graph showing quantification of NF-$_K$B-positive nuclei in the liver sections. The experiments were reproduced twice independently and representative images are shown. Results are presented as mean±SEM (n=10). Statistically significant differences between groups are marked as asterisks; ***P<0.001; n.s.: nonsignificant.

FIG. 14A is a graph showing body weight changes of NCR nude mice that received intravenous injection of free cisplatin (2 mg Pt kg$^{-1}$), MNCs (2 mg Pt kg$^{-1}$) or HA-EGCG at an equivalent dose to that of MNCs (39.2 mg kg$^{-1}$). The black arrows indicate the time points of injection (days 0, 4, 7, and 11).

FIG. 14B is a bar chart graph showing ALT levels in the blood harvested at the 14-d endpoint. Results are presented as mean±SEM (n=10). Statistically significant differences between groups are marked as asterisks; *P<0.05; P<0.01; *P<0.001; n.s.: nonsignificant.

FIG. 14C is a bar chart graph showing levels of blood urea nitrogen in the blood harvested at the 14-d endpoint. Results are presented as mean±SEM (n=10). Statistically significant differences between groups are marked as asterisks; *P<0.05; P<0.01; *P<0.001; n.s.: nonsignificant.

FIG. 14D is a bar chart graph showing Na$^+$ in the blood harvested at the 14-d endpoint. Results are presented as mean±SEM (n=10). Statistically significant differences between groups are marked as asterisks; *P<0.05; P<0.01; *P<0.001; n.s.: nonsignificant.

FIG. 15 is a graph showing size distribution of HA-EGCG/carboplatin MNCs prepared at various feeding concentrations of HA-EGCG. The feeding concentration of carboplatin was 0.6 mg mL$^{-1}$.

FIG. 16 is a graph showing drug loading efficiency and loading content of HA-EGCG/carboplatin MNCs prepared at various feeding concentrations of HA-EGCG. The feeding concentration of carboplatin was 0.6 mg mL$^{-1}$.

FIG. 17 is a graph showing size distribution of HA-EGCG/oxaliplatin MNCs prepared at various feeding concentrations of HA-EGCG. The feeding concentration of oxaliplatin was 0.6 mg mL$^{-1}$.

FIG. 18 is a graph showing drug loading efficiency and loading content of HA-EGCG/oxaliplatin MNCs prepared at various feeding concentrations of HA-EGCG. The feeding concentration of oxaliplatin was 0.6 mg mL$^{-1}$.

FIG. 19 is a graph showing dose-response cytotoxicity curves for SKOV-3 cells treated with free carboplatin or HA-EGCG/carboplatin MNCs.

FIG. 20 is a graph showing dose-response cytotoxicity curves for HCT116 cells treated with free oxaliplatin or HA-EGCG/oxaliplatin MNCs.

DETAILED DESCRIPTION OF DRAWINGS

Referring to FIG. 1, there is shown a schematic diagram of a method 100 to form a nanocomplex 10 of the present application. A functionalized hyaluronic acid-flavonoid conjugate 2 is first formed where the flavonoid 4 is conjugated with the functionalized hyaluronic acid 6. In aqueous solutions, the conjugate 2 self-assembles 102 to form a functionalized hyaluronic acid-flavonoid conjugate micelle 8. This self-assembly process is driven mainly by the hydrophobic interactions of the flavonoid molecules. The solution of the functionalized hyaluronic acid-flavonoid conjugate micelle 8 is then mixed with an aqueous solution of a metal-containing compound at a suitable temperature 104 to form the nanocomplex 10 where the metal-containing compound 12 is encapsulated by the flavonoid within the core of the nanocomplex 10.

EXAMPLES

Non-limiting examples of the invention and comparative examples will be further described in greater detail by reference to specific Examples, which should not be construed as in any way limiting the scope of the invention.

Example 1—Formation of HA-EGCG/Cisplatin MNCs

The method of FIG. 1 was used here to form nanocomplexes 10 of HA-EGCG/cisplatin MNCs.
Synthesis of HA-EGCG Conjugates
HA (M$_w$=20 kDa) was purchased from Lifecore Biomedical (of Chaska, Minn. of the United States of America). HA was first modified with thiol group at the reducing end to form the functionalized hyaluronic acid 6. Typically, HA (500 mg) and cystamine dihydrochloride (600 mg, 5.3 mmol) were dissolved in 30 mL of 0.1 M borate buffer (pH 8.5) containing 0.4 M sodium chloride (NaCl, obtained from Sigma-Aldrich of St. Louis of Missouri of the United States of America). The reaction mixture was stirred for 2 hours at 25° C. To this solution, 628 mg, 10 mmol of sodium cyanoborohydride (NaBH$_3$CN, obtained from Sigma-Aldrich of St. Louis of Missouri of the United States of America) dissolved in 20 mL of 0.1 M borate buffer (pH 8.5) was slowly added. The mixture was incubated at 37° C. for 5 days while stirring. Then, 20 mL of 0.5 M Tris(2-carboxyethyl)phosphine hydrochloride (TCEP, obtained from Tokyo Chemical Industry of Tokyo, Japan) solution was added and stirred for 2 hours at 25° C. to generate free thiol groups. The resulting mixture was transferred to dialysis tubes with a molecular weight cutoff of 1,000 Da. The tubes were dialyzed against 0.1 M sodium chloride solution for 2 days, 25% ethanol for 1 day, and deionized water for 1 day under nitrogen atmosphere. The purified solution was lyophilized to obtain thiol end-modified HA. After lyophilization, the final product was kept at −20° C. in the dark. The amount of free thiol groups in HA was determined by Ellman's assay using 5,5'-dithiobis(2-nitrobenzoic acid) (Ellman's reagent) and $_L$-cysteine (both obtained from Sigma-Aldrich of St. Louis of Missouri of the United States of America) as a standard. The efficiency of thiol end-modification of HA was higher than 98%, as determined by Ellman's assay. The yield of the thiol end-modified HA was 93%.

For conjugation reaction, flavonoid 4 such as epigallocatechin gallate (EGCG, >95% purity, obtained from Kurita Water Industries of Tokyo, Japan at 1.1 g, 2.4 mmol) was dissolved in 180 mL of 10 mM phosphate-buffered saline (PBS, pH 7.4) containing 2 mM of sodium pyruvate (obtained from Invitrogen of Carlsbad of California of the United States of America). Thiol end-modified HA (600 mg, 0.03 mmol) was dissolved in 60 mL of PBS solution containing 2 mM of sodium pyruvate. Then, the solution was added dropwise to a stirred solution of EGCG. The pH of the mixture was adjusted to 7.4 by dropwise addition of 1 M sodium hydroxide. The mixture was stirred for 6 hours at 25° C. The pH of the mixture was adjusted to 6 by dropwise addition of 1% acetic acid solution. The resultant solution was transferred to dialysis tubes with a molecular weight cutoff of 2,000 Da. The tubes were extensively dialyzed against 25% ethanol for 1 day, and deionized water for 3 days under nitrogen atmosphere. The purified solution was lyophilized to obtain a conjugate micelle 8 such as EGCG-terminated HA conjugate micelle. UV-visible spectra of HA-EGCG conjugate micelles were measured on a Hitachi U-2810 spectrophotometer. The extent of EGCG conjugation was determined by measuring the absorbance of EGCG at 274 nm. The degree of EGCG conjugation was approximately 100%. The structure of the product was further confirmed by $^1$H NMR spectroscopy. $^1$H NMR ($D_2O$): δ 2.1 (s, —C=$OCH_3$ from HA), 2.9-3.0 (d, H-4 of C ring), 3.3-4.0 (m, protons of HA), 4.45 and 4.55 (d, HA anomeric proton), 5.60-5.85 (s, H-2 and H-3 of C ring), 6.1-6.3 (s, H-6 and H-8 of A ring), 6.7 (s, H-6' of B ring), 6.95 (s, H-2" and H-6" of D ring). Yield: 93%. $^1$H NMR spectroscopy revealed that a single HA molecule was covalently attached at the pyrogallol moiety of EGCG.

Preparation of HA-EGCG/Cisplatin MNCs

HA-EGCG conjugates and a metal-containing compound 12 such as cisplatin (obtained from Sigma-Aldrich of St. Louis of Missouri of the United States of America) were dissolved in deionized water at initial concentrations of 5 mg $mL^{-1}$ and 2 mg $mL^{-1}$, respectively. To prepare HA-EGCG/cisplatin MNCs, 5 mL of HA-EGCG solution was mixed with 1.25 mL of cisplatin solution. The mixture was incubated for 3 days at 37° C. on an orbital shaker at 50 rpm in a dark place. The three-days incubation period was chosen because the maximal level of cisplatin loading was achieved at this time point. As EGCG is able to form stable coordination bonds and hydrogen bonds with cisplatin, it was hypothesized that cisplatin would be efficiently incorporated in the interior of the micellar nanocomplexes where multiple EGCG molecules exist. To remove uncomplexed cisplatin and HA-EGCG, the resulting mixture was transferred to Amicon Ultra-15 centrifugal filters (obtained from Merck Millipore Corporation of Darmstadt of Germany) with a molecular weight cutoff of 50,000 Da. HA-EGCG/cisplatin MNCs were retrieved by centrifugation for 10 minutes at 2,000×g at 20° C. and then purified by repeating dispersion in deionized water and centrifugation three times. The purified MNCs were resuspended in 10 mL of deionized water and stored at 4° C. until use.

Comparative Example 1—Formation of HA/Cisplatin Complexes

HA/cisplatin complexes were prepared by mixing 5 mg $mL^{-1}$ HA solution with 2 mg $mL^{-1}$ cisplatin solution and subsequently incubated for 3 days at 37° C. on an orbital shaker at 50 rpm in a dark place. To remove uncomplexed cisplatin and HA, the resulting mixture was transferred to Amicon Ultra-15 centrifugal filters with a molecular weight cutoff of 50,000 Da. HA/cisplatin MNCs were retrieved by centrifugation for 10 minutes at 2,000×g at 20° C. and then purified by repeating dispersion in deionized water and centrifugation three times. The purified complexes were resuspended in 10 mL of deionized water and stored at 4° C. until use.

Comparative Example 2—Formation of PEG-EGCG/Cisplatin MNCs

For formation of PEG-EGCG/cisplatin MNCs, PEG-EGCG was prepared via an aldehyde-mediated reaction. 0.35 g of aldehyde-terminated PEG (PEG-CHO, $M_w$ 5 kDa, obtained from NOF Co. of Japan) and 0.65 g EGCG were separately dissolved in a mixture of acetic acid, water and dimethyl sulfoxide (DMSO). The reaction was started with the dropwise addition of the PEG-CHO solution at 20° C., pH 2 under a nitrogen atmosphere for 48 hours. The resulting products were dialyzed (molecular weight cut-off (MWCO) of 3500) and lyophilized to give the PEG-EGCG conjugates.

PEG-EGCG conjugates and cisplatin were dissolved in deionized water at a concentration of 6 mg $mL^{-1}$ and 1.2 mg $mL^{-1}$, respectively. PEG-EGCG solution (1 mL) was added to cisplatin solution (1 mL), and the resulting mixture was vortexed for 20 minutes. The solution was transferred to dialysis tubes with a molecular weight cutoff of 1,000 Da. The tubes were dialyzed against deionized water for 2 days, with the water replaced every 12 hours.

Example 2—Characterization Assays

Hydrodynamic Diameter

The hydrodynamic diameters of HA-EGCG conjugate micelles, HA-EGCG/cisplatin MNCs and HA/cisplatin complexes were measured using a particle size analyzer (Zetasizer Nano ZS, Malvern Instruments, UK). All measurements were performed in triplicate.

As shown in FIG. 2A-1, HA-EGCG conjugates self-assembled into conjugate micelles with an average diameter of 109±30 nm in deionized water. This self-assembly process was driven by the hydrophobic interactions of the EGCG moieties above the critical micelle concentration of about 38.5 µM. Incubation of the micelles with cisplatin at 37° C. for 3 days led to the formation of HA-EGCG/cisplatin MNCs with an average diameter of 57±6 nm, indicative of the shrinkage of HA-EGCG conjugate micelles after incorporation of cisplatin. It is unexpected that after encapsulation of cisplatin, the micellar nanocomplexes actually become smaller than the conjugate micelles. This dramatic size change was likely attributed to the intra-micellar cross-linking of adjacent HA-EGCG polymer chains via the coordination bonds and hydrogen bonds with cisplatin. Notably, HA-EGCG/cisplatin MNCs were much smaller than HA/cisplatin complexes formed by mixing unmodified HA with cisplatin in the same conditions. Inhomogeneous aggregates with a bimodal size distribution peaking at 91±16 nm and 396±49 nm were observed from the aqueous dispersion of HA/cisplatin complexes. This result suggested that a simple mixing of unmodified HA with cisplatin caused the ligand exchange reaction of Pt(II) in an uncontrolled manner, leading to the formation of relatively large HA/cisplatin complexes over a broad size range. The presence of the EGCG thus unexpectedly led to stabilizing of the nanocomplex, resulting in smaller nanocomplexes over a narrower size distribution. It is to be noted here that a simple mixing of EGCG and cisplatin would likely cause the formation of non-homogeneous complexes in an uncontrolled manner.

FIG. 2A-2 (when compared with FIG. 2A-1) shows that the PEG-EGCG/cisplatin MNCs were much larger than HA-EGCG/cisplatin MNCs. In addition, PEG-EGCG/cisplatin MNCs had a broad particle size distribution with mean diameters up to 1 micron, which are not ideal for passive tumor targeting via the enhanced permeability and retention (EPR) effect. This result revealed that HA-EGCG/cisplatin MNCs had a more compact micellar nanostructure than PEG-EGCG/cisplatin MNCs. It was also noteworthy that the PEG-EGCG/cisplatin MNCs had a larger size than PEG-EGCG micelles, indicative of an increase in the particle size following cisplatin encapsulation. Hence, although both MNCs contain EGCG that are able to form coordination bonds and hydrogen bonds with cisplatin, the HA-EGCG/cisplatin MNCs have the smallest particle size among the various types of complexes or micellar nanocomplexes investigated here, which is unexpected.

Transmission Electron Microscopy

Transmission electron microscopy (TEM) images were taken on a PEI Tecnai G2 F20 transmission electron microscope.

From the TEM images, it can be seen that the HA-EGCG/cisplatin MNCs have a spherical core/shell structure, in which the cisplatin-loaded micellar core was surrounded by a polymeric shell layer (FIG. 2B and FIG. 2C). This distinctive structure revealed that the majority of cisplatin was encapsulated in the core of HA-EGCG/cisplatin MNCs where multiple EGCG molecules existed. In contrast, HA/cisplatin complexes consisted of irregularly shaped objects of two different sizes, where each object contained scattered black dots, indicating that cisplatin molecules were randomly distributed within the complexes (FIG. 2D and FIG. 2E).

Platinum Content

The platinum (Pt) content of HA-EGCG/cisplatin MNCs and HA/cisplatin complexes was analyzed by inductively coupled plasma mass spectrometry (ICP-MS). Briefly, 100 µL of each sample was treated with 504 of 65% (v/v) nitric acid at 25° C. for 24 hours. The resultant solution was diluted with 9.85 mL of deionized water and then analyzed using an Elan DRC II ICP mass spectrometer (Perkin Elmer, Waltham of Massachusetts of the United States of America). Based on the platinum content, the drug content and loading efficiency of the samples can be obtained. The drug content and loading efficiency can be calculated by the following equations below:

Drug content (%)=(Amount of loaded cisplatin/ Weight of complexes)×100

Loading efficiency (%)=(Amount of loaded cisplatin/ Feeding amount of cisplatin)×100

The drug loading content indicates the structural composition of nanocomplexes in terms of the mass of cisplatin per nanocomplex while the drug loading efficiency indicates how efficient the drug-encapsulation process was under a specific set of conditions. The "feeding amount of cisplatin" is the initial mass of cisplatin used per drug-encapsulation process.

As presented in FIG. 3A, HA-EGCG/cisplatin MNCs exhibited remarkably higher drug content and loading efficiency than HA/cisplatin complexes. HA-EGCG/cisplatin MNCs showed about 4.8-fold and 23.5-fold improvement in the drug content and loading efficiency, respectively, relative to HA/cisplatin complexes. The existence of EGCG-enriched core was likely responsible for the efficient encapsulation of cisplatin through the formation of stable coordination bonds and hydrogen bonds. It was also noteworthy that the drug content and loading efficiency of HA-EGCG/cisplatin MNCs were much higher than those of PEG-EGCG/cisplatin MNCs. This result was probably ascribed to the enhanced incorporation of cisplatin molecules in the compactly assembled nanostructure of HA-EGCG/cisplatin MNCs.

The drug content and particle size of HA-EGCG/cisplatin MNCs could be modulated by varying the concentration of the added cisplatin and HA-EGCG (FIG. 3B). HA-EGCG/cisplatin MNCs made from cisplatin (0.4 mg mL$^{-1}$) and HA-EGCG (4 mg mL$^{-1}$) were selected because they had relatively high drug content and the smallest size ideal for passive tumor targeting via the EPR effect.

Drug Release Study

HA-EGCG/cisplatin MNCs, HA/cisplatin complexes and free cisplatin solution containing the same quantity of Pt (5 µg) were transferred to a Float-A-Lyzer dialysis tube with a molecular weight cutoff of 1,000 Da (Spectrum Laboratories, Compton of California of the United States of America). The dialysis tube was immersed in total 30 mL of 10 mM PBS (pH 7.4). The dialysis tube was then incubated at 37° C. on an orbital shaker at 50 rpm. To examine the effect of hyaluronidase treatment on drug release kinetics, a mixture of HA-EGCG/cisplatin MNCs (5 µg Pt) and hyaluronidase at various concentrations (15 units/mL, 120 units/mL or 600 units/mL) was transferred to a dialysis tube with a molecular weight cutoff of 1,000 Da. The dialysis tube was then immersed in total 30 mL of 100 mM phosphate buffer (pH 6) at 37° C. At predetermined time points, the amount of cisplatin released in the medium was determined by ICP-MS as described above.

The release kinetics of cisplatin from HA-EGCG/cisplatin MNCs and HA/cisplatin complexes in 10 mM phosphate-buffered saline (PBS, pH 7.4) at 37° C. were examined to investigate their stabilities at physiological pH and temperature. HA-EGCG/cisplatin MNCs, HA/cisplatin complexes and free cisplatin solution containing the same quantity of Pt (5 µg) were transferred to dialysis tubes and then immersed in PBS. As expected, free cisplatin was completely released from the dialysis tube within 6 hours (FIG. 4). Notably, HA-EGCG/cisplatin MNCs released around 43% of the loaded cisplatin for 5 days in a sustained manner while nearly 75% of the drug content was liberated from HA/cisplatin complexes during the same period. This rapid drug leakage was caused by the dissociation of HA/cisplatin complexes via the replacement of the carboxylate ligand of Pt(II) with the chloride ion in PBS. HA-EGCG/cisplatin MNCs exhibited superior stability over HA/cisplatin complexes because cisplatin was encapsulated within MNCs were examined coordination bonds and hydrogen bonds. It was anticipated that HA-EGCG/cisplatin MNCs with superior physiological stability would remain more stable during blood circulation and thus have a higher opportunity to accumulate in tumors preferentially via the EPR effect.

As shown in FIG. 5, the rate of drug release gradually increased with raising the concentration of HAase, suggesting that the HA-EGCG MNCs liberated the loaded cisplatin molecules upon HAase-mediated dissociation. Hence, it is possible that cell-internalized HA-EGCG/cisplatin MNCs would release the cisplatin payload in response to the endosomal HAase. The HAase-responsive property of HA-EGCG/cisplatin MNCs would be advantageous to achieve tumor-selective drug delivery where rapid transport of cisplatin into the nucleus of a cancer cell is achieved (leading to formation of cisplatin-DNA adducts that are essential for cancer call death) while minimizing a premature drug leakage during systemic circulation.

Quantification of Intracellular Platinum Accumulation

Human ovarian carcinoma SKOV-3 cells and human colorectal carcinoma HCT116 cells (that express high levels of CD44) were maintained in McCoy's 5A medium supplemented with 10% (v/v) fetal bovine serum (FBS) and 1% (v/v) penicillin/streptomycin. Ad5-transformed human embryonic kidney HEK293T cells (that do not express CD44, used as a comparison) were maintained in Dulbecco's modified Eagle's medium supplemented with 10% (v/v) FBS and 1% (v/v) penicillin/streptomycin. SKOV-3, HCT116 and HEK293T cells were seeded on 6-well plates at a density of $2 \times 10^5$ cells per well and then cultivated for 24 hours at 37° C. These cells were incubated for 24 hours with 2 mL of serum-free medium containing HA-EGCG/cisplatin MNCs at a final Pt concentration of 80 μM. The cells were rinsed twice with 2 mL of ice-cold PBS, harvested by trypsinization and then counted using a hemocytometer. After centrifugation, the cell pellet was digested in 100 μL of 65% (v/v) nitric acid at 25° C. for 24 hours. The lysate solution was diluted with 2.9 mL of deionized water and then filtered through a 0.45 μm syringe filter. Cellular Pt levels were determined by ICP-MS and expressed in pg Pt/$10^5$ cells.

To ascertain whether the cellular entry of the HA-EGCG/cisplatin MNCs occurred via CD4-mediated endocytosis, a competition assay was performed where SKOV-3, HCT116 and HEK293T cells seeded on 6-well plates ($2 \times 10^5$ cells per well) were incubated with 1 mL of serum-free media containing free HA at a concentration of 10 mg mL$^{-1}$ for 1 hour at 37° C. to block CD44. The cells were further incubated for 24 hours with HA-EGCG/cisplatin MNCs at a final Pt concentration of 80 μM. The cells were rinsed, harvested and then counted using a hemocytometer. Cellular Pt levels were determined by ICP-MS as described above.

FIG. 6 shows the platinum content of the cells treated for 24 hours with HA-EGCG/cisplatin MNCs. The SKOV-3 and HCT116 cells exhibited much higher levels of cellular platinum content than HEK293T cells. This result proved that HA-EGCG/cisplatin MNCs could internalize into CD44-overexpressing cancer cells more efficiently than CD44-negative normal cells. To investigate whether the cellular uptake of MNCs occurred via CD44-mediated endocytosis, the cells were pre-treated with excess amounts of free HA in order to block CD44. Indeed, the pretreatment of free HA significantly decreased the platinum content of SKOV-3 and HCT116 cells whereas it had little influence on that of HEK293T cells. The decreased platinum content of SKOV-3 and HCT116 cells can be explained by a reduction in CD44-mediated endocytosis of MNCs in the presence of free HA. Hence the above results revealed that HA-EGCG/cisplatin MNCs efficiently delivered the drug payload into CD44-overexpressing cancer cells in a target-specific manner.

Cytotoxicity Evaluation

SKOV-3, HCT116 and HEK293T cells were seeded on black-walled 96-well plates at a density of $2.5 \times 10^3$ cells per well and then cultivated for 24 hours at 37° C. These cells were treated for 24 hours with 200 μL of serum-free medium containing HA-EGCG/cisplatin MNCs or HA/cisplatin complexes at a final platinum concentration of 80 μM. After the medium was changed to fresh serum-free medium, the cells were further incubated for another 48 hours. Cell viability was evaluated using the AlamarBlue® cell viability assay reagent (Life Technologies, Carlsbad of California of the United States of America) which measures cellular metabolic reduction. Briefly, 50 μL of serum-free medium containing 50% (v/v) AlamarBlue® reagent was added to each well of the 96-well plates. After incubation for 3 hours at 37° C., the cellular fluorescence was measured using a Tecan Infinite microplate reader (Tecan Group, Switzerland) with an excitation wavelength at 530 nm and an emission wavelength at 590 nm. The cell viability was expressed as percentages derived from the fluorescence intensity from the treated cells relative to untreated cells.

FIG. 7 shows the cancer cell-killing effect of HA-EGCG/cisplatin MNCs and HA/cisplatin complexes. HA-EGCG/cisplatin MNCs were found to induce enhanced killing of SKOV-3 and HCT116 cells compared to HEK293T cells. The selective cancer cell-killing effect of MNCs was likely ascribed to their efficient internalization by the cancer cells via CD44-mediated endocytosis. On the other hand, HA/cisplatin complexes did not exhibit selectivity; these complexes were highly toxic to both cancer and normal cells probably due to their poor stability and rapid drug leakage under physiological environment.

Evaluation of Cellular Caspase-3/7 Activities

SKOV-3, HCT116 and HEK293T cells were seeded on white-walled 96-well plates at a density of $2.5 \times 10^3$ cells per well and then cultivated for 24 hours at 37° C. These cells were treated for 24 hours with 200 μL of serum-free medium containing HA-EGCG/cisplatin MNCs at various concentrations. After the medium was changed to fresh serum-free medium, the cells were further incubated for another 48 hours. Cellular caspase-3/7 activities were evaluated using the Caspase-Glo® 3/7 assay kit (Promega Corporation, Madison of Wisconsin of the United States of America). Briefly, 100 μL of the Caspase-Glo® 3/7 assay reagent was added to each well of the 96-well plates. After incubation for 1 hour at 37° C., the cellular luminescence was measured using a Tecan Infinite microplate reader (Tecan Group, Switzerland). Relative caspase-3/7 activities were determined from the luminescence signal of each sample normalized to the total number of viable cells. The results were expressed as fold change in caspase-3/7 expression levels relative to the untreated cells.

The cellular caspase-3 and caspase-7 activities show the extent of apoptotic death of the cancer cells treated with HA-EGCG/cisplatin MNCs. Both caspases 3 and 7 are known as crucial proteases involved in the early stage of apoptosis. As presented in FIG. 8, the treatment of HA-EGCG/cisplatin MNCs increased the caspase-3/7 expression levels in SKOV-3 and HCT116 cells in a dose-dependent manner, indicating that the internalized cisplatin triggered caspase-3/7 dependent apoptotic pathways in the cancer cells. It was noteworthy that SKOV-3 and HCT116 cells exhibited remarkably higher caspase-3/7 activities than HEK293T cells following MNC treatment. The enhanced intracellular uptake of HA-EGCG/cisplatin MNCs was probably responsible for the pronounced caspase activities observed from the cancer cells. Collectively, these results demonstrated that HA-EGCG/cisplatin MNCs enabled targeted delivery of cisplatin to CD44-overexpressing cancer cells and consequently induced their apoptotic death by triggering the activation of caspases.

Pharmacokinetic and Biodistribution Studies

All animal experiments were performed according to the protocols approved by the IACUC at the Biological Resource Centre, Singapore. Female athymic NCR nude mice (CrTac:Ncr-Foxn1$^{nu}$, 5-6 weeks old) were inoculated subcutaneously with $1 \times 10^7$ SKOV-3 cells suspended in 100 µL of PBS and 100 µL of Matrigel (BD Bioscience, of the United States of America) in the right flank. When the tumor volume reached approximately 120-150 mm³, the mice were injected intravenously via the tail vein with 200 µL of an isotonic dextrose solution (5% w/v) containing free cisplatin, MNCs or HA/cisplatin complexes at a dose of 2 mg Pt kg$^{-1}$. At predetermined time points, blood and organs were collected (4 mice per time point). The collected plasma and organs were decomposed in 65% (v/v) nitric acid at 60° C. for 2 hours, and the platinum concentration was measured by ICP-MS.

FIG. 9 depicts the pharmacokinetic profiles of free cisplatin, HA-EGCG/cisplatin MNCs and HA/cisplatin complexes injected intravenously in the human ovarian carcinoma SKOV-3 tumor-bearing mice above. It is well known that the antitumor efficacy of free cisplatin is severely limited by its short circulation time and insufficient tumor accumulation. The vast majority of the administered cisplatin was eliminated from the bloodstream within a few hours probably due to its fast renal clearance. Notably, MNCs exhibited a remarkable improvement in blood circulation over free cisplatin and HA/cisplatin complexes. The significantly slower clearance of MNCs relative to HA/cisplatin complexes was attributable to their smaller size and higher physiological stability favorable for prolonged blood circulation.

FIG. 10 shows the biodistribution of free cisplatin, HA-EGCG/cisplatin MNCs and HA/cisplatin complexes following intravenous administration in the subcutaneous SKOV-3 xenograft model above. HA-EGCG/cisplatin MNCs delivered a significantly larger dose of cisplatin (5.56±0.98% ID/g) into the tumor mass when compared with free cisplatin (1.53±0.48% ID/g) and HA/cisplatin complexes (0.97±0.50% ID/g). The enhanced tumor targeting of HA-EGCG/cisplatin MNCs was probably originated from their preferential tumor accumulation via the EPR effect as well as CD44-mediated uptake into the tumor cells.

Antitumor Efficacy Study in a Subcutaneous Xenograft Model

Female NCR mice bearing a subcutaneous SKOV-3 human ovarian cancer xenograft (120-150 mm³) were randomly allocated to different treatments (10 mice per group). The mice received intravenous injection of free cisplatin (1 mg Pt kg$^{-1}$), HA-EGCG/cisplatin MNCs (1 mg Pt kg$^{-1}$) or HA-EGCG at an equivalent dose to that of MNCs (19.6 mg kg$^{-1}$) on days 0, 7, and 14. An isotonic dextrose solution (5% w/v) was used as a control. The tumor volume (mm³) was calculated from the following formula: volume=(length× width²)/2. In addition, a change in the body weight in the course of treatment was monitored as a measure of systemic toxicity.

As depicted in FIG. 11, HA-EGCG/cisplatin MNCs suppressed the tumor growth more effectively than free cisplatin and HA-EGCG. The mean tumor volumes of HA-EGCG/cisplatin MNC-treated mice (181.2±75.1 mm³) were significantly smaller than those of the control mice (405.2±141.6 mm³) and the mice treated with free cisplatin (299.7±117.7 mm³) on day 38. The preferential tumor accumulation of HA-EGCG/cisplatin MNCs was probably responsible for their strong tumor-inhibitory effect.

Although free cisplatin slightly delayed the tumor growth, it was highly toxic. The mice that received three injections of free cisplatin lost about 17.8% of their initial body weight (FIG. 12). Even after cisplatin administration was stopped, nearly 3 weeks were required for recovery of the body weights of the mice back to normal levels. This serious weight loss was likely caused by cisplatin-induced hepatotoxicity and nephrotoxicity. In contrast, notable weight loss was not observed in HA-EGCG/cisplatin MNC-treated mice throughout the course of treatment, suggesting that HA-EGCG/cisplatin MNCs did not exert systemic toxicity despite their pronounced antitumor efficacy. Collectively, these results demonstrated that HA-EGCG/cisplatin MNCs exhibited superior in vivo antitumor efficacy over free cisplatin without severe toxicities.

Blood Chemistry Analysis and Histological Examination

The athymic NCR mice that received different treatments were sacrificed to collect blood, tumor, and organs 38 days after the first treatment. For blood chemistry analysis, blood samples were collected in heparinized tubes and then examined using the Vetscan VS2 blood chemistry analyzer (Abaxis Inc., of California of the United States of America). The levels of alkaline phosphatase (ALP), alanine aminotransferase (ALT) and other serum markers were examined. The excised tumors and organs were fixed with neutral buffered formalin, embedded in paraffin blocks, and then sectioned for hematoxylin and eosin (H&E) staining.

The alkaline phosphatase ALP and ALT levels are shown in FIG. 13A and FIG. 13B. Cisplatin-treated mice developed severe liver injury, as evident from the elevated levels of ALP and ALT. In contrast, the ALP and ALT levels in HA-EGCG/cisplatin MNC-treated mice were not significantly different from those in the control mice, suggesting that HA-EGCG/cisplatin MNCs did not cause any noticeable damage to the liver. This result was surprising because HA-EGCG/cisplatin MNCs induced greater platinum accumulation in the liver (2.52±0.40% ID/g) than free cisplatin (1.31±0.25% ID/g) as presented in FIG. 10. It is believed that the antioxidant activity of HA-EGCG delivered by the HA-EGCG/cisplatin MNCs might contribute to the prevention of cisplatin-induced hepatotoxicity in HA-EGCG/cisplatin MNC-treated mice.

To examine the extent of cisplatin-induced liver injury, immunohistochemistry was performed on the liver sections using a rabbit anti-I$_K$B, C-21 polyclonal antibody and a rabbit anti-NF-$_K$B p50 NLS polyclonal antibody (Santa Cruz Biotechnology of Dallas, Tex. of the United States of America). The sections were stained with DAB substrate and then counterstained with hematoxylin. The percentage of I$_K$B$_a$-positive cells was quantified using the Image-Pro Plus software (Media Cybernetics, of Rockville, Md. of the United States of America). The extent of nuclear translocation of NF-$_K$B was calculated by dividing the number of NF-$_K$B-positive nuclei by the total number of nuclei in each field.

It has been reported that cisplatin-derived reactive oxygen species are involved in the activation of NF-κB signaling pathway. Immunohistochemical staining showed a remarkable degradation of I$_K$B$_a$ with a concomitant nuclear localization of NF-$_K$B in the liver of cisplatin-treated mice when compared to those of the other groups (FIG. 13C). This suggested that free cisplatin treatment stimulated the generation of reactive oxygen species in the liver and thus activated NF-κB signaling pathway responsible for oxidative liver damage. These observations were further supported by the quantitative analysis of the percentage of I$_K$B$_a$-positive cells and NF-$_K$B-positive nuclei (FIG. 13D and FIG. 13E). In contrast to cisplatin, administration of HA-EGCG/cisplatin MNCs did not trigger the activation of NF-$_K$B signaling pathway in the liver. These findings suggested that the antioxidant HA-EGCG, delivered along with cisplatin, effectively abrogated NF-$_\kappa$B signaling cascade by scavenging cisplatin-derived reactive oxygen species and thus provided a fail-safe protection to avoid off-target hepatotoxicity of cisplatin.

In Vivo Acute Toxicity Study

To evaluate the in vivo acute toxicity of high-dose cisplatin and HA-EGCG/cisplatin MNC, athymic NCR nude mice were randomly allocated to different treatments for 14 days: free cisplatin (2 mg kg$^{-1}$, i.v., twice/week), HA-EGCG/cisplatin MNCs (2 mg kg$^{-1}$, i.v., twice/week), HA-EGCG at an equivalent dose to that of HA-EGCG/cisplatin MNCs (39.2 mg kg$^{-1}$, i.v., twice/week) and isotonic dextrose solution as a control. The weekly cisplatin dose (4 mg Pt kg$^{-1}$ per week) used for this toxicity study was 4 times higher than that for the antitumor efficacy study (1 mg Pt kg$^{-1}$ per week).

The free cisplatin-treated mice showed more severe weight loss than HA-EGCG/cisplatin MNC-treated mice (FIG. 14A). Blood chemistry analysis at the 14-days endpoint revealed that the cisplatin-treated mice had markedly increased levels of ALT (FIG. 14B), blood urea nitrogen (FIG. 14C) and Na$^+$ (FIG. 14C), indicative of the severe hepatotoxicity and nephrotoxicity of high-dose cisplatin. In contrast, the mice treated with high-dose HA-EGCG/cisplatin MNC displayed similar ALT (FIG. 14B), blood urea nitrogen (FIG. 14C) and Na$^+$ (FIG. 14D) levels to those of healthy mice. These results revealed that the combination of cisplatin and EGCG in a single nanocarrier greatly attenuated the cisplatin-induced hepatotoxicity and nephrotoxicity.

CONCLUSION

This application shows that that HA-EGCG/cisplatin MNCs had a smaller size, higher drug-loading capacity and superior stability under physiological environment than HA/cisplatin complexes. While HA/cisplatin complexes were highly toxic to both cancer and normal cells, HA-EGCG/cisplatin MNCs differential cancer cell-killing effect by delivering their payload into CD44-overexpressing cancer cells in a target-specific manner. Pharmacokinetic and biodistribution studies revealed that HA-EGCG/cisplatin MNCs exhibited prolonged circulation and enhanced tumor accumulation than HA/cisplatin complexes upon intravenous administration. Furthermore, HA-EGCG/cisplatin MNCs achieved potent antitumor efficacy without severe toxicities in a subcutaneous xenograft model. Given the targeting ability and fail-safe mechanism to avoid off-target toxicity of cisplatin, HA-EGCG/cisplatin MNCs will be broadly applicable for the treatment of various types of cancers expressing high levels of CD44.

Example 3—Preparation of HA-EGCG/carboplatin and HA-EGCG/oxaliplatin MNCs

Carboplatin and oxaliplatin are now assessed here as another example of the metal-containing compound. Carboplatin, the second generation analog of cisplatin, has emerged as a clinically important anticancer drug because it has fewer side effects than cisplatin. However, the dose-limiting toxicities such as myelosuppression and neurotoxicity are still associated with the use of carboplatin. Oxaliplatin has been widely used for the treatment of colorectal cancers because it exhibits stronger antitumor activity against colon cancer cells than its predecessors, cisplatin and carboplatin.

HA-EGCG and either carboplatin or oxaliplatin were mixed in deionized water at various concentrations and then incubated for 3 days at 37° C. in a dark place. The mixture was transferred to Amicon Ultra-15 centrifugal filters (molecular weight cutoff: 50,000 Da). The resulting mixture was transferred to Amicon Ultra-15 centrifugal filters with a molecular weight cutoff of 50,000 Da. MNCs were retrieved by centrifugation for 10 minutes at 2,000×g at 20° C. and then purified by repeating dispersion in deionized water and centrifugation three times. The hydrodynamic diameters of MNCs were measured using a particle size analyzer (Zetasizer Nano ZS, Malvern Instruments, UK). All measurements were performed in triplicate. The drug loading content and loading efficiency of MNCs were analyzed by ICP-MS using an Elan DRC II ICP mass spectrometer (PerkinElmer, USA).

Dynamic light scattering analysis was conducted to examine the effect of the feeding concentrations of HA-EGCG on the formation of HA-EGCG/carboplatin MNCs (FIG. 15). The smallest HA-EGCG/carboplatin MNCs were produced when the feeding concentrations of HA-EGCG was 6 mg mL$^{-1}$. The drug content and loading efficiency were determined by measuring the Pt content using ICP-MS (FIG. 16). The drug loading efficiency gradually increased with the feeding concentrations of HA-EGCG. The highest drug content and loading efficiency were obtained when the feeding concentrations of HA-EGCG was 10 mg mL$^{-1}$.

Dynamic light scattering analysis revealed that the formation of HA-EGCG/oxaliplatin MNCs was dependent on the feeding concentrations of HA-EGCG (FIG. 17). The smallest HA-EGCG/oxaliplatin MNCs were produced when the feeding concentrations of HA-EGCG was 6 mg mL$^{-1}$. The drug content and loading efficiency were investigated by ICP-MS (FIG. 18). The highest drug loading efficiency was obtained when the feeding concentrations of HA-EGCG was 8 mg mL$^{-1}$. MNCs produced at this condition were chosen for the cytotoxicity study.

Evaluation of Cytotoxic Effect of HA-EGCG/Carboplatin MNCs

SKOV-3 cells were seeded on black-walled 96-well plates at a density of 2.5×10$^3$ cells per well and then cultivated for 24 hours at 37° C. These cells were treated for 3 days with 200 µL of serum-free medium containing HA-EGCG/carboplatin MNCs at various platinum concentrations. For comparison, the cells were also treated with free carboplatin at equivalent platinum concentrations. Cell viability was evaluated using the AlamarBlue® cell viability assay reagent which measures cellular metabolic reduction. Briefly, 50 µL of serum-free medium containing 50% (v/v) AlamarBlue® reagent was added to each well of the 96-well plates. After incubation for 3 hours at 37° C., the cellular fluorescence was measured using a Tecan Infinite microplate reader (Tecan Group, Switzerland) with an excitation wavelength at 530 nm and an emission wavelength at 590 nm. The cell viability was expressed as percentages derived from the fluorescence intensity from the treated cells relative to untreated cells.

The dose-response cytotoxicity study revealed that HA-EGCG/carboplatin MNCs were more effective in killing SKOV-3 cells than free carboplatin (FIG. 19). The enhanced anticancer effect of MNCs was likely attributed to their efficient internalization by the cancer cells via CD44-mediated endocytosis.

Evaluation of Cytotoxic Effect of HA-EGCG/Oxaliplatin MNCs

HCT116 cells were seeded on black-walled 96-well plates at a density of 2.5×10$^3$ cells per well and then cultivated for 24 hours at 37° C. These cells were treated for 3 days with 200 µL of serum-free medium containing HA-EGCG/oxaliplatin MNCs at various Pt concentrations. For comparison, the cells were also treated with free oxaliplatin at equivalent Pt concentrations. Cell viability was evaluated using the AlamarBlue® cell viability assay reagent which measures cellular metabolic reduction. Briefly, 50 μL of serum-free medium containing 50% (v/v) AlamarBlue® reagent was added to each well of the 96-well plates. After incubation for 3 hours at 37° C., the cellular fluorescence was measured using a Tecan Infinite microplate reader (Tecan Group, Switzerland) with an excitation wavelength at 530 nm and an emission wavelength at 590 nm. The cell viability was expressed as percentages derived from the fluorescence intensity from the treated cells relative to untreated cells.

Notably, HA-EGCG/oxaliplatin MNCs were more effective in killing human colorectal carcinoma HCT116 cells than free oxaliplatin (FIG. 20). This result suggests the potential utility of HA-EGCG/oxaliplatin MNCs for the treatment of colorectal cancers.

INDUSTRIAL APPLICABILITY

The nanocomplex may be used as a delivery agent or delivery system to deliver the metal-containing compound to a subject. The delivery agent may selectively target a desired tumour site. The nanocomplex may be used in an anticancer therapy program or may be used in addition to chemotherapy. The nanocomplex may be used as an anticancer medicament.

The nanocomplex may be used for sustained release of the metal-containing compound when administered to a cell.

The nanocomplex may have a smaller size, higher drug loading capacity, better stability, more prolonged circulation, enhanced tumor accumulation, more potent antitumor efficacy and/or reduced toxicity as compared to known delivery systems or when compared to a complex of (unmodified) hyaluronic acid with the metal-containing compound(es). This may be due to the synergistic combination of the flavonoid and the metal-containing compound that enhance the antitumour efficacy while suppressing toxicity from the metal-containing compound.

The nanocomplex may be formed from a simple mixing of a solution of a functionalized hyaluronic acid-flavonoid conjugate with a solution of the metal-containing compound. The nanocomplex may be formed from a spontaneous self-assembly of functionalized hyaluronic acid-flavonoid conjugate with the metal-containing compound.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method for forming a nanocomplex having a functionalized hyaluronic acid shell and a core comprising epigallocatechin gallate encapsulating a metal-containing compound selected from the group consisting of cisplatin, oxaliplatin, and carboplatin, the method comprising a step of mixing a solution of the metal-containing compound with a solution of a conjugate of the functionalized hyaluronic acid and the epigallocatechin gallate, thereby forming a reaction solution, wherein:

said functionalized hyaluronic acid shell is a thiol-functionalized hyaluronic acid shell, when the metal-containing compound is cisplatin, the cisplatin has a concentration of 0.4 mg/mL to 1.0 mg/mL in the reaction solution and the conjugate of the functionalized hyaluronic acid and the epigallocatechin gallate has a concentration of 4 mg/mL to 10 mg/mL in the reaction solution, when the metal-containing compound is oxaliplatin, the oxaliplatin has a concentration of 0.6 mg/mL in the reaction solution, and the conjugate of the functionalized hyaluronic acid and the epigallocatechin gallate has a concentration of 8 mg/mL in the reaction solution, and when the metal containing compound is carboplatin, the carboplatin has a concentration of 0.6 mg/mL in the reaction solution, and the conjugate of the functionalized hyaluronic acid and the epigallocatechin gallate has a concentration of 10 mg/mL in the reaction solution.

2. The method of claim 1, further comprising a step of isolating the formed nanocomplex.

3. The method of claim 2, further comprising a step of purifying the isolated nanocomplex.

4. The method of claim 1, wherein said conjugate of the functionalized hyaluronic acid and the epigallocatechin gallate has the structure I:

Structure 1

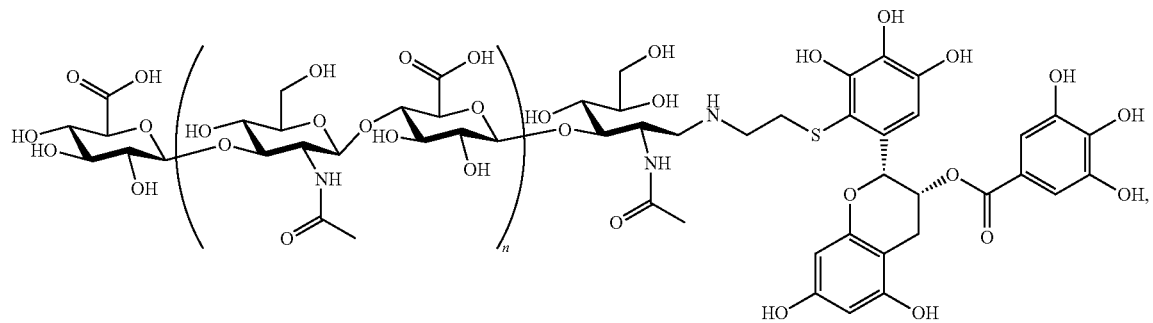

wherein n is an integer from 1 to 15,000.

5. The method of claim 1, wherein said conjugate of the functionalized hyaluronic acid and the epigallocatechin gallate is prepared from hyaluronic acid having an average molecular weight of 20 kDa.

6. A method for forming a nanocomplex having a functionalized hyaluronic acid shell and a core comprising epigallocatechin gallate encapsulating cisplatin, the method comprising a step of mixing a solution of cisplatin with a solution of a conjugate of the functionalized hyaluronic acid and the epigallocatechin gallate, thereby forming a reaction solution, wherein:
    said functionalized hyaluronic acid shell is a thiol-functionalized hyaluronic acid shell, and
    the concentration of cisplatin in the reaction solution is 0.4 mg/mL to 1.0 mg/mL and concentration of the conjugate of the functionalized hyaluronic acid and the epigallocatechin gallate in the reaction solution is 4 mg/ML to 10 mg/mL.

7. The method of claim 6, further comprising a step of isolating the formed nanocomplex.

8. The method of claim 7, further comprising a step of purifying the isolated nanocomplex.

9. The method of claim 6, wherein said conjugate of the functionalized hyaluronic acid and the epigallocatechin gallate has the structure I:

Structure 1

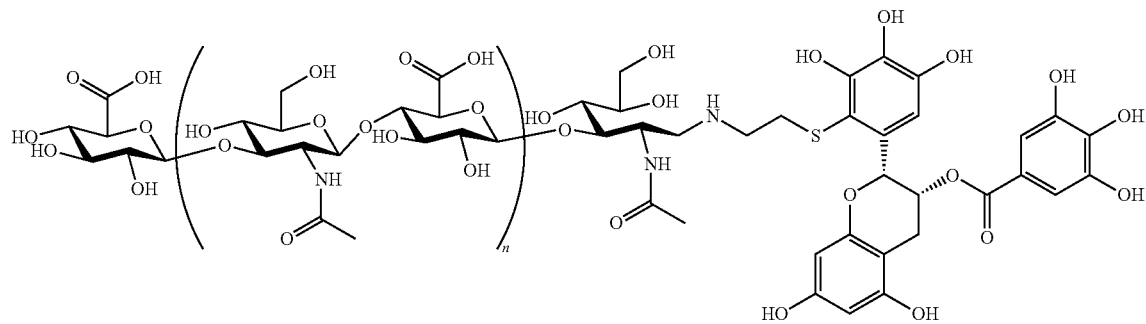

wherein n is an integer from 1 to 15,000.

10. The method of claim 6, wherein said conjugate of the functionalized hyaluronic acid and the epigallocatechin gallate is prepared from hyaluronic acid having an average molecular weight of 20 kDa.

11. A method for forming a nanocomplex having a functionalized hyaluronic acid shell and a core comprising epigallocatechin gallate encapsulating oxaliplatin, the method comprising a step of mixing a solution of oxaliplatin with a solution of a conjugate of the functionalized hyaluronic acid and the epigallocatechin gallate, thereby forming a reaction solution, wherein:
    said functionalized hyaluronic acid shell is a thiol-functionalized hyaluronic acid shell, and
    the concentration of oxaliplatin in the reaction solution is 0.6 mg/mL and concentration of the conjugate of the functionalized hyaluronic acid and the epigallocatechin gallate in the reaction solution is 8 mg/mL.

12. The method of claim 11, further comprising a step of isolating the formed nanocomplex.

13. The method of claim 12, further comprising a step of purifying the isolated nanocomplex.

14. The method of claim 11, wherein said conjugate of the functionalized hyaluronic acid and the epigallocatechin gallate has the structure I:

Structure 1

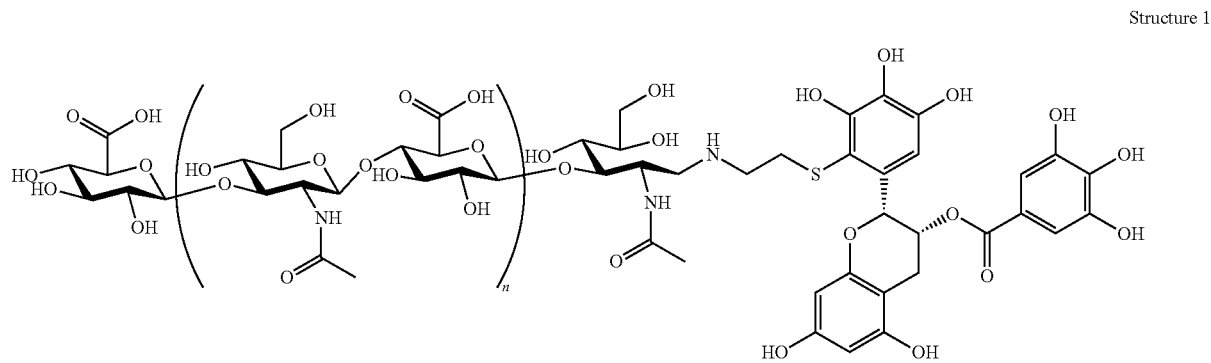

wherein n is an integer from 1 to 15,000.

15. The method of claim 11, wherein said conjugate of the functionalized hyaluronic acid and the epigallocatechin gallate is prepared from hyaluronic acid having an average molecular weight of 20 kDa.

16. A method for forming a nanocomplex having a functionalized hyaluronic acid shell and a core comprising epigallocatechin gallate encapsulating carboplatin, the method comprising a step of mixing a solution of carboplatin with a solution of a conjugate of the functionalized hyaluronic acid and the epigallocatechin gallate, thereby forming a reaction solution, wherein:
said functionalized hyaluronic acid shell is a thiol-functionalized hyaluronic acid shell, and
the concentration of carboplatin in the reaction solution is 0.6 mg/mL and concentration of the conjugate of the functionalized hyaluronic acid and the epigallocatechin gallate in the reaction solution is 10 mg/mL.

17. The method of claim 16, further comprising a step of isolating the formed nanocomplex.

18. The method of claim 17, further comprising a step of purifying the isolated nanocomplex.

19. The method of claim 16, wherein said conjugate of the functionalized hyaluronic acid and the epigallocatechin gallate has the structure I:

Structure 1

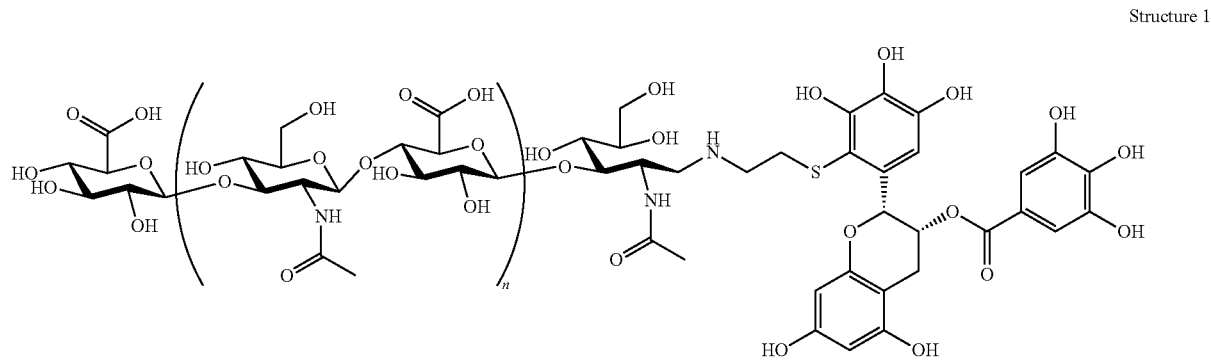

wherein n is an integer from 1 to 15,000.

20. The method of claim 16, wherein said conjugate of the functionalized hyaluronic acid and the epigallocatechin gallate is prepared from hyaluronic acid having an average molecular weight of 20 kDa.

* * * * *